US011529358B2

(12) United States Patent
Bassell et al.

(10) Patent No.: US 11,529,358 B2
(45) Date of Patent: Dec. 20, 2022

(54) TREATMENT OF CONDITIONS ASSOCIATED WITH MYOTONIC DYSTROPHY

(71) Applicants: EMORY UNIVERSITY, Atlanta, GA (US); UNIVERSITY OF FLORIDA RESEARCH FOUNDATION, INC., Gainesville, FL (US)

(72) Inventors: Gary Bassell, Atlanta, GA (US); Andrew Jenkins, Decatur, GA (US); David B. Rye, Dunwoody, GA (US); Maurice Scott Swanson, Gainesville, FL (US); Eric Tzy-Shi Wang, Gainesville, FL (US); Lyndon Lien, Hillsborough, CA (US)

(73) Assignees: Emory University, Atlanta, GA (US); University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 16/612,192

(22) PCT Filed: May 10, 2018

(86) PCT No.: PCT/US2018/032114
§ 371 (c)(1),
(2) Date: Nov. 8, 2019

(87) PCT Pub. No.: WO2018/209119
PCT Pub. Date: Nov. 15, 2018

(65) Prior Publication Data
US 2021/0023091 A1    Jan. 28, 2021

Related U.S. Application Data

(60) Provisional application No. 62/504,364, filed on May 10, 2017, provisional application No. 62/527,782, filed on Jun. 30, 2017.

(51) Int. Cl.
*A61K 31/5517* (2006.01)
*A61P 21/00* (2006.01)

(52) U.S. Cl.
CPC .......... *A61K 31/5517* (2013.01); *A61P 21/00* (2018.01)

(58) Field of Classification Search
CPC ........................... A61K 31/5517; A61P 21/00
See application file for complete search history.

(56) References Cited

FOREIGN PATENT DOCUMENTS

| WO | WO-2009114740 A2 * | 9/2009 | ............. A61K 9/006 |
|---|---|---|---|
| WO | 2012151343 | 11/2012 | |
| WO | 2015160766 | 10/2015 | |

OTHER PUBLICATIONS

Atack, Gabaa Receptor Subtype-Selective Modulators. II. α5-Selective Inverse Agonists for Cognition Enhancement, Current topics in medicinal chemistry, vol. 11, No. 9, Nov. 2010, pp. 1203-1214.
Ballard et al., RO4938581, a Novel Cognitive Enhancer Acting at GABAA Alpha5 Subunit-Containing Receptors, Psychopharmacology, vol. 202, Nos. 1-3, Jan. 2009, pp. 207-223.
Bednar et al., Plasma and Cerebrospinal Fluid (CSF) Pharmacokinetics of CP-457,920, a Selective Alpha 5 GABA-A Receptor Inverse Agonist in Young, Healthy Volunteers, Clinical Pharmacology & Therapeutics, vol. 75, No. 2, Feb. 26, 2004, p. 30.
Billiard et al., Idiopathic Hypersomnia, Sleep Medicine Reviews, vol. 29, Sep. 3, 2015, pp. 23-33.
Chambers et al., 6,7-Dihydro-2-benzothiophen-4(5H)-ones: A Novel Class of GABA-A α5 Receptor Inverse Agonists, Journal of Medicinal Chemistry, vol. 45, No. 6, Feb. 12, 2002, pp. 1176-1179.
Chambers et al., An Orally Bioavailable, Functionally Selective Inverse Agonist at the Benzodiazepine Site of GABAA Alpha5 Receptors with Cognition Enhancing Properties, Journal of Medicinal Chemistry, vol. 47, No. 24, Nov. 18, 2004, pp. 5829-5832.
Chambers et al., Identification of a Novel, Selective GABA(A) Alpha5 Receptor Inverse Agonist Which Enhances Cognition, Journal of Medicinal Chemistry, vol. 46, No. 11, May 22, 2003, pp. 2227-2240.
Charizanis et al., Muscleblind-Like 2 Mediated Alternative Splicing in the Developing Brain and Dysregulation in Myotonic Dystrophy, Neuron, vol. 75, No. 3, Aug. 9, 2012, pp. 437-450.
Goodwin et al., MBNL Sequestration by Toxic RNAs and RNA Misprocessing in the Myotonic Dystrophy Brain, Cell Reports, vol. 12, No. 7, Aug. 18, 2015, pp. 1159-1168.
Katz et al., Analysis and Design of RNA Sequencing Experiments for Identifying Isoform Regulation, Nature Methods, vol. 7, No. 12, Dec. 2010, pp. 1009-1015.
Laberge et al., Sleep Complaints in Patients with Myotonic Dystrophy, Journal of Sleep Research, vol. 13, No. 1, Feb. 23, 2004, pp. 95-100.
Liquori et al., Myotonic Dystrophy Type 2 Caused by a CCTG Expansion in Intron 1 of ZNF9, Science, vol. 293, No. 5531, Aug. 3, 2001, pp. 864-867.

(Continued)

*Primary Examiner* — Brenda L Coleman
(74) *Attorney, Agent, or Firm* — Emory Patent Group

(57) ABSTRACT

Disclosed are methods of treating a disorder or disease associated with myotonic dystrophy. Methods of treating a CNS dysfunction and/or cognitive impairment associated with myotonic dystrophy in a subject comprising administering a therapeutically effective amount of a GABAA receptor antagonist or inverse agonist to the subject are disclosed. Methods of treating a myotonic dystrophy associated disease or disorder caused by mis-splicing of GABRG2 in a subject comprising administering a therapeutically effective amount of a GABAA receptor antagonist or inverse agonist to the subject are disclosed. Methods of improving cognitive function or alertness in a subject having myotonic dystrophy comprising administering a therapeutically effective amount of a GABAA receptor antagonist or inverse agonist to the subject are disclosed. Examples of the GABAA receptor antagonist or inverse agonist include flumazenil, clarithromycin, a fluoroquinolone, picrotoxin, bicuculline, gabazine, cicutoxin, oenan-thotoxin, pentylenetetrazol, Ro15-4513, sarmazenil, amentoflavone, zinc, and any combination thereof.

10 Claims, 6 Drawing Sheets

(56) References Cited

OTHER PUBLICATIONS

International Application No. PCT/US2018/032114, International Preliminary Report on Patentability dated Nov. 21, 2019, 8 pages.
International Application No. PCT/US2018/032114, International Search Report and Written Opinion dated Jul. 24, 2018, 10 pages.
Quinlan et al., Mice Lacking the Long Splice Variant of the Gamma 2 Subunit of the GABA(A) Receptor are More Sensitive to Benzodiazepines, Pharmacology Biochemistry and Behavior, vol. 66, No. 2, Jun. 2000, pp. 371-374.
Romigi et al., Sleep-Wake Cycle and Daytime Sleepiness in the Myotonic Dystrophies, Journal of Neurodegenerative Diseases, vol. 2013, 2013, 13 pages.
Rye et al., Modulation of Vigilance in the Primary Hypersomnias by Endogenous Enhancement of GABAA Receptors, Science Translational Medicine, vol. 4, No. 161, Nov. 21, 2012, pp. 1-12.
Salva et al., Sleep Disorders in Childhood-Onset Myotonic Dystrophy Type 1, Neuromuscular Disorders, vol. 16, Nos. 9-10, Oct. 2006, pp. 564-570.
Skolnick et al., [3H] RY 80: A High-affinity, Selective Ligand for Gamma-Aminobutyric Acida Receptors Containing Alpha-5 Subunits, The Journal of Pharmacology and Experimental Therapeutics, vol. 283, No. 2, Nov. 1, 1997, pp. 488-493.
Sternfeld et al., Selective, Orally Active γ-Aminobutyric AcidA α5 Receptor Inverse Agonists as Cognition Enhancers, Journal of Medicinal Chemistry, vol. 47, No. 9, May 2004, pp. 2176-2179.
Street et al., Synthesis and Biological Evaluation of 3-Heterocyclyl-7,8,9,10-tetrahydro-(7,10-ethano)-1,2,4-triazolo[3,4-a] phthalazines and Analogues as Subtype-Selective Inverse Agonists for the GABAAα5 Benzodiazepine Binding Site, Journal of Medicinal Chemistry, vol. 47, No. 14, May 28, 2004, pp. 3642-3657.
Trotti et al., Flumazenil for the Treatment of Refractory Hypersomnolence: Clinical Experience with 153 Patients, Journal of Clinical Sleep Medicine, vol. 12, No. 10, Oct. 15, 2016, pp. 1389-1394.

\* cited by examiner

TREATMENT OF CONDITIONS ASSOCIATED WITH MYOTONIC DYSTROPHY

CROSS REFERENCE TO RELATED APPLICATIONS

This application claims the benefit of priority to U.S. Provisional Application 62/504,364, filed May 10, 2017, and U.S. Provisional Application 62/527,782, filed Jun. 30, 2017, the disclosures of each are incorporated by reference herein in their entireties.

GOVERNMENT SUPPORT

The invention was made with government support under Grant No. OD017865, NS058901, NS089719, NS055015, and AR046799 awarded by the National Institutes of Health. The government has certain rights in the invention.

FIELD

This disclosure relates generally to compositions and methods for treating conditions associated with myotonic dystrophy, particularly to using a GABAA receptor antagonist or inverse agonist for treating conditions associated with myotonic dystrophy.

BACKGROUND

Myotonic dystrophy (DM or Steinert's disease) is a multisystemic disorder often characterized by neuromuscular weakness, muscle degeneration and myotonia or delayed muscle relaxation due to repetitive action potentials in myofibers. Numerous multisystemic symptoms are observed in DM patients, including over 100 biological processes negatively affected in their muscle cells. Manifestations of DM can include heart conduction defects, ocular cataracts, hypogonadism, and nervous system dysfunction. DM patients also often suffer from cardiac conduction defects, smooth muscle involvement, hypersomnia, cataracts, abnormal glucose response, and, in males, premature balding and testicular atrophy. Romigi, et al., *J. Neurodegener. Dis.,* 2013, 1-3.

Myotonic dystrophy can be of two forms, type I (DM1) and type II (DM2), which are clinically, histopathologically, and genetically distinct forms of myotonic dystrophy. DM1 is caused by a CTG expansion in the 3' untranslated region of the dystrophia myotonica-protein kinase gene (DMPK) on chromosome 19q13. DM2 is found to be caused by a CCTG expansion located in intron 1 of the zinc finger protection 9 (ZNF9) gene on chromosome 3q21. Liguori et al., *Science,* 2001, 293(5531):864-867. Up to 70-80% adults diagnosed with DM1 experience unintended sleep and daytime sleepiness. This impairment in vigilant wakefulness is the most common non-muscular symptom. See Quera Salva et al., *Neuromuscular Disorders,* 2006, 16:564-570.

There is currently no cure for or treatment specific to myotonic dystrophy, and the clinical focus is on managing one or more of the complications of the disease. There is a continuing need for compositions and methods which can treat conditions associated with myotonic dystrophy. The compositions and methods disclosed herein address these and other needs.

SUMMARY

Disclosed herein are methods of treating conditions associated with myotonic dystrophy. The particular myotonic dystrophy disorder can be a type I or a type II disorder. As described herein, conditions associated with myotonic dystrophy can include nervous system dysfunction and impairment in cognition (i.e., decrements in speed of processing information). In some aspects, methods of treating a central nervous system (CNS) dysfunction and/or cognitive impairment associated with myotonic dystrophy in a subject comprising administering a therapeutically effective amount of a $GABA_A$ receptor antagonist or inverse agonist to the subject are disclosed. The CNS dysfunction and/or cognitive impairment can be a neurodevelopmental dysfunction, a neurofunctional dysfunction, a neurodegenerative dysfunction, or a combination thereof. For example, the CNS dysfunction and/or cognitive impairment can include anhedonia, impaired executive function, reduced alertness, reduced motivation, reduced arousal, apathy, fatigue, hypersomnia, excessive daytime sleepiness, or a combination thereof.

In other aspects, methods of treating a myotonic dystrophy associated disease or disorder caused by mis-splicing of GABRG2 in a subject comprising administering a therapeutically effective amount of a $GABA_A$ receptor antagonist or inverse agonist to the subject are disclosed. In certain embodiments, methods of treating a myotonic dystrophy associated disease or disorder caused by mis-splicing of GABRG2 in a subject comprising administering a therapeutically effective amount of a $GABA_A$ receptor antagonist or inverse agonist to the subject are provided, wherein the subject has a higher 2S/2L isoform ratio than a subject with a normal 2S/2L isoform ratio. In certain embodiments, methods of treating a myotonic dystrophy associated disease or disorder caused by mis-splicing of GABRG2 in a subject comprising administering a therapeutically effective amount of a $GABA_A$ receptor antagonist or inverse agonist to the subject are provided, wherein the subject has a higher 2S/2L isoform ratio than a subject with a normal 2S/2L isoform ratio, and wherein the $GABA_A$ receptor antagonist or inverse agonist is flumazenil. Normal and elevated 2S/2L isoform ratio can be assessed as described in Quinlan, et al., *Pharmacol. Biochem. Behav.,* 2000; 66:371-4.

In another aspect, the disclosure provides a method of treating a subject identified as having a GABRG2 defect, comprising administering to said subject an effective amount of a compound or pharmaceutical composition herein, such that said subject is treated for said disorder or disease.

In still other aspects, methods of improving cognitive function in a subject having myotonic dystrophy comprising administering a therapeutically effective amount of a $GABA_A$ receptor antagonist or inverse agonist to the subject are disclosed. In further aspects, methods of improving alertness in a subject having myotonic dystrophy comprising administering a therapeutically effective amount of a $GABA_A$ receptor antagonist or inverse agonist to the subject are disclosed.

In still other aspects, methods of treating hypersomnia in a subject comprising administering a therapeutically effective amount of a $GABA_A$ receptor antagonist or inverse agonist to the subject are disclosed. The subject may have myotonic dystrophy.

In another aspect, the disclosure provides a method of treating a subject suffering from or susceptible to a disorder or disease identified herein, wherein the subject has been identified as in need of treatment for the disorder or disease, comprising administering to said subject in need thereof, an effective amount of a compound or pharmaceutical composition herein, such that said subject is treated for the disorder or disease. The disorder or disease may be myotonic dystrophy.

As disclosed herein, the condition associated with myotonic dystrophy can be treated by administering a $GABA_A$ receptor antagonist or inverse agonist. In some embodiments, the $GABA_A$ receptor antagonist or inverse agonist can include flumazenil, clarithromycin, a fluoroquinolone, picrotoxin, bicuculline, gabazine, cicutoxin, oenanthotoxin, or combinations thereof. In some embodiments, the $GABA_A$ receptor antagonist or inverse agonist can be flumazenil.

The $GABA_A$ receptor antagonists or inverse agonists used in the treatments disclosed herein can be administered to the subject by intravenous injection, intramuscular injection, subcutaneous injection, sublingual administration, intranasal (inhalation), oral administration, transdermal administration, or a combination thereof. For example, the $GABA_A$ receptor antagonist or inverse agonist can be administered sublingually as a tablet, powder, film strip, capsule, lozenge, or troche. In other examples, the $GABA_A$ receptor antagonist or inverse agonist can be administered transdermally as an ointment, emulsion, lotion, cream, solution, gel, or patch. In certain embodiments, the $GABA_A$ receptor antagonist or inverse agonist can be administered sublingually or transdermally. The $GABA_A$ receptor antagonist or inverse agonist can be administered as a unit dose. In some cases, the unit dose can be administered daily for one, two, three or more times. In certain embodiments, the $GABA_A$ receptor antagonist or inverse agonist can be administered transdermally. In certain embodiments, the $GABA_A$ receptor antagonist or inverse agonist can be administered as a patch.

In some embodiments, the therapeutically effective amount of $GABA_A$ receptor antagonist or inverse agonist administered can be in an amount to reduce total habitual sleep time per day, compared to a subject that was not administered a $GABA_A$ receptor antagonist or inverse agonist. In other embodiments, the therapeutically effective amount of $GABA_A$ receptor antagonist or inverse agonist administered can be in an amount to improve alertness, mental processing, and cognitive function, compared to a subject that was not administered a $GABA_A$ receptor antagonist or inverse agonist. In still other embodiments, the therapeutically effective amount of $GABA_A$ receptor antagonist or inverse agonist administered can be in an amount to improve the subject's processing speed by a factor of two or greater, as determined by the Symbol Digit Modalities Test, compared to a subject not being administered a $GABA_A$ receptor antagonist or inverse agonist. In some embodiments, the therapeutically effective amount of $GABA_A$ receptor antagonist or inverse agonist administered can be from 5 mg to 1,000 mg. For example, the therapeutically effective amount of flumazenil administered can be from 5 mg to 40 mg or from 5 mg to 20 mg. The therapeutically effective amount of clarithromycin administered can be up to 3,000 mg daily, e.g., 2,000 mg daily, or 1,000 mg daily.

In some embodiments, the therapeutically effective amount of $GABA_A$ receptor antagonist or inverse agonist can be administered in a slow-release formulation. In some embodiments, the therapeutically effective amount of $GABA_A$ receptor antagonist or inverse agonist can be administered in a slow-release formulation to a subject in need thereof in the period immediately upon waking. In some embodiments, the $GABA_A$ receptor antagonist or inverse agonist can be administered in combination with an additional therapeutic agent. In some embodiments, the $GABA_A$ receptor antagonist or inverse agonist can be administered in combination with an additional therapeutic agent, wherein the $GABA_A$ receptor antagonist or inverse agonist is flumazenil. In some embodiments, the $GABA_A$ receptor antagonist or inverse agonist can be administered in combination with an additional therapeutic agent, wherein the $GABA_A$ receptor antagonist or inverse agonist is flumazenil and the additional therapeutic agent is a stimulant. In some embodiments, the $GABA_A$ receptor antagonist or inverse agonist can be administered in combination with an additional therapeutic agent, wherein the $GABA_A$ receptor antagonist or inverse agonist is flumazenil and the additional therapeutic agent is modafinil.

Additional advantages of the disclosed compositions and methods will be set forth in part in the description which follows, and in part will be obvious from the description. The advantages of the disclosed compositions and methods will be realized and attained by means of the elements and combinations particularly pointed out in the appended claims. It is to be understood that both the foregoing general description and the following detailed description are exemplary and explanatory only and are not restrictive of the disclosed systems and methods, as claimed.

BRIEF DESCRIPTION OF THE FIGURES

The accompanying figures, which are incorporated in and constitute a part of this specification, illustrate several aspects described below.

FIG. 2A shows the distribution of the length of time elapsed between a visual stimulus and user input by pressing a button before flumazenil treatment. The lapses are >500 milliseconds. FIG. 2B shows the same distribution following 2.0 mg intravenously administered flumazenil, in the same individual. There is a dramatic decrease in time elapsed between visual stimulus and user input. FIG. 2C shows the total lapses in attention is decreased in subject 1 (labeled as subject 3 in this graph) following flumazenil treatment at 2 different doses. FIG. 2D shows the subjective sense of self reported sleepiness on the Stanford sleepiness scale is reduced at 2 different doses of flumazenil in subject 1 (labeled as subject 3 in this graph).

FIG. 4A shows the proportion of total GABRG2 mRNA that contains the Gamma 2L exon relative to total (2L+2S) in wild type or MBNL2 knockout mouse cortex is plotted for 3 mice per genotype. FIG. 4B shows the proportion of total GABRG2 mRNA that contains the Gamma 2L exon relative to total (2L+2S) in wild type or MBNL1+ MBNL2 double knockout mouse brain, plotted as 3 mice per genotype. FIG. 4C shows the proportion of total GABRG2 mRNA that contains the 2L exon relative to total is plotted for 4 non-DM1 and 4 DM1 human postmortem cortex samples. All splicing inclusion levels were estimated by analyses of RNAseq transcriptome data.

DETAILED DESCRIPTION

Figure 1:
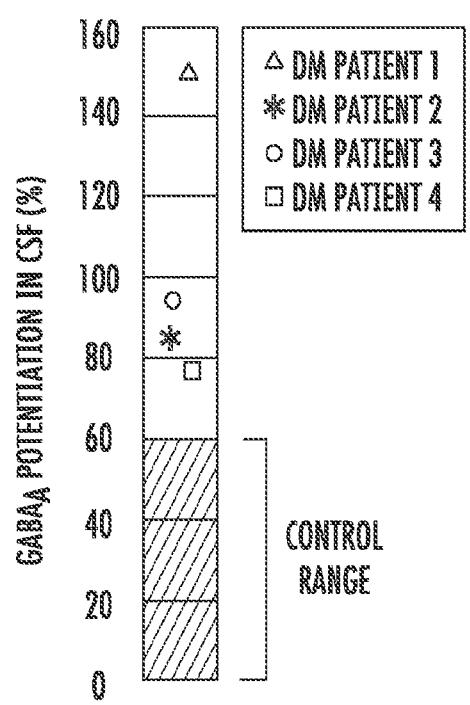
FIG. 1 is a graph showing enhancement of GABRG2s containing receptors by CSF from 4 DM1 patients measured in vitro by patch clamp electrophysiology in HEK293T cells. All 4 are above what would be observed in the control range of activity from control CSF (N=14).
Figure 2A:
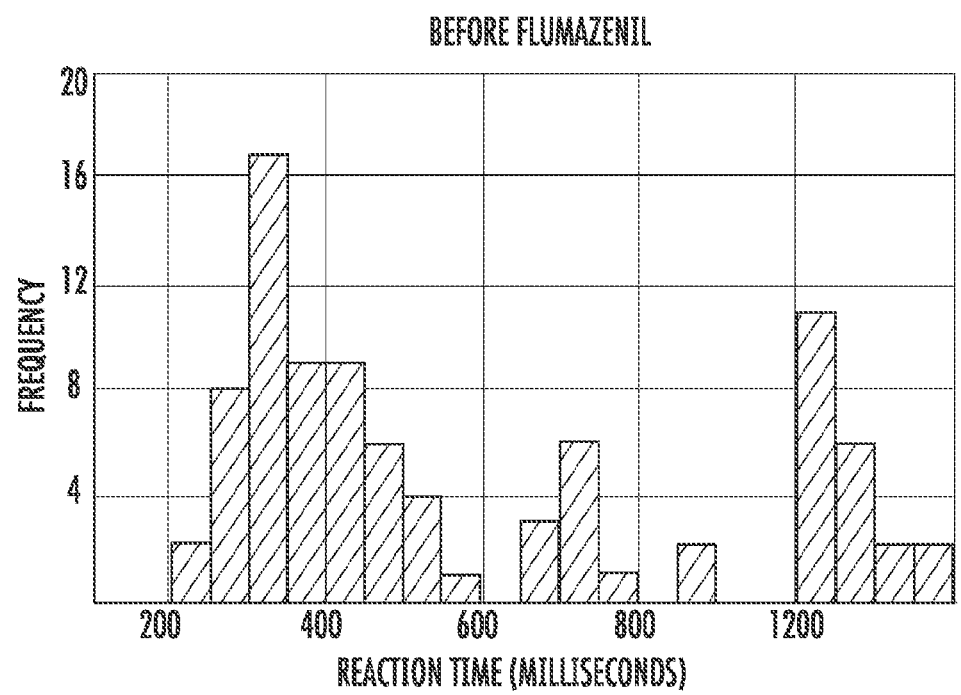
FIGS. 2A-2D are graphs showing objective and subjective metrics upon treatment with intravenously administered flumazenil in DM subject 1.
Figure 2B:
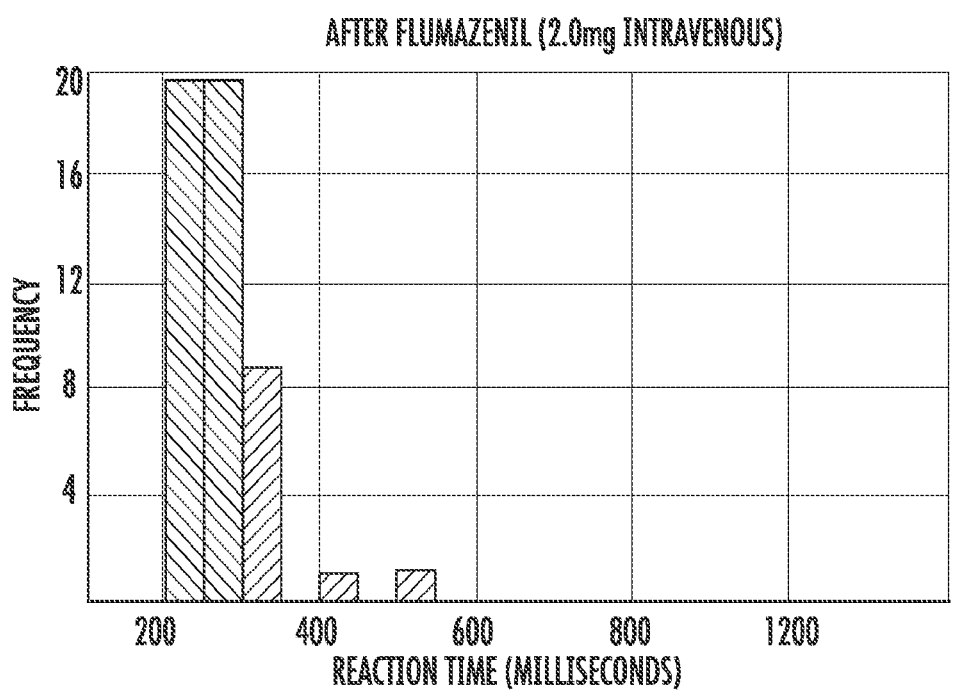
Figure 2C:
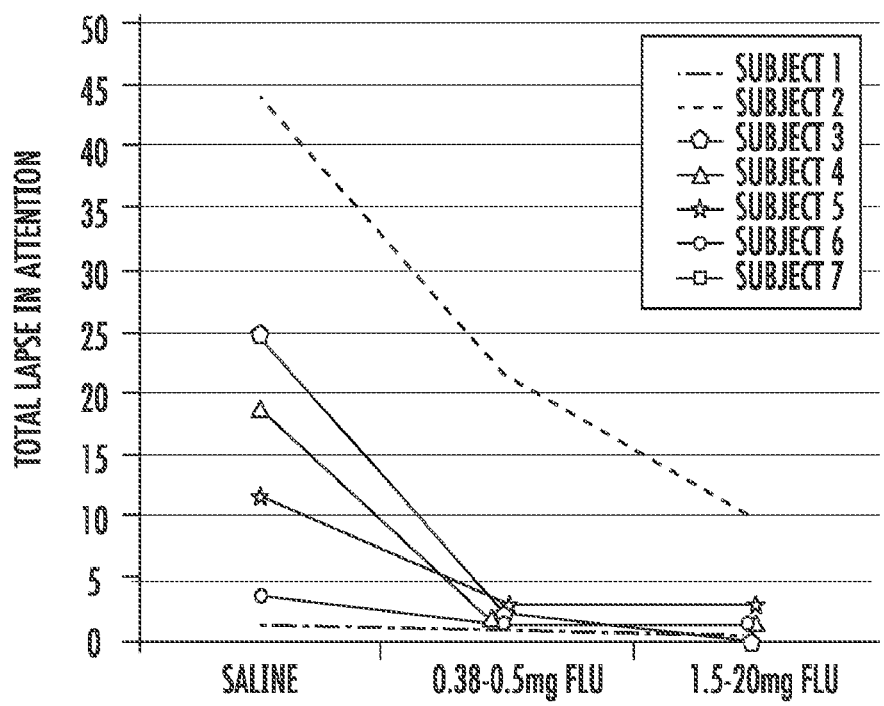
Figure 2D:
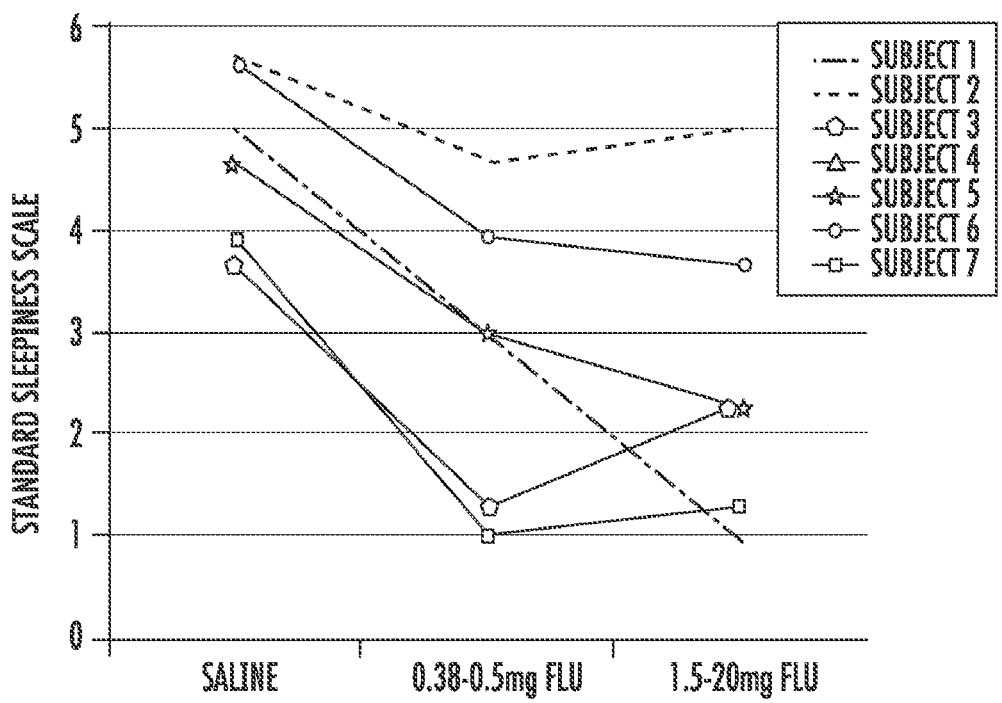

Compositions and methods for treating conditions associated with myotonic dystrophy are disclosed herein. The compositions can include a $GABA_A$ receptor antagonist or inverse agonist for treating conditions associated myotonic dystrophy.

Before the present compositions and/or methods are described, it is to be understood that this disclosure is not limited to specific active agents, such as specific sleep promoting compounds or particular compounds that enhance mental acuity, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a $GABA_A$ receptor antagonist or inverse agonist" includes mixtures of $GABA_A$ receptor antagonists or inverse agonists; reference to "an antagonist" includes mixtures of antagonists; reference to "the compound" includes mixtures of two or more such compounds, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

By "treat" or other forms of the word, such as "treated", "treating", or "treatment," is meant to administer a composition or to perform a method in order to reduce or prevent a particular characteristic or event (e.g., a condition associated with myotonic dystrophy). The term "control" is used synonymously with the term "treat." To treat a condition associated with myotonic dystrophy, according to the methods described herein, the treatment does not necessarily provide therapy for the underlying pathology that is causing the myotonic dystrophic sensation. Treatment of a condition associated with myotonic dystrophy can be purely symptomatic.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method, including those delineated herein).

It is understood that throughout this specification the identifiers "first" and "second" are used solely to aid in distinguishing the various components, features, and steps of the disclosed subject matter. The identifiers "first" and "second" are not intended to imply any particular order, amount, preference, or importance to the components or steps modified by these terms.

The term "pharmaceutically acceptable" as used herein refers to a component that is compatible with other ingredients of a pharmaceutical composition or formulation and is suitable for use in contact with tissues of a subject without undue toxicity, irritation, allergic response, immunogenicity or other complications, commensurate with a reasonable benefit/risk ratio.

As used herein, the abbreviation "GABA" refers to gamma-aminobutyric acid.

As used herein, the abbreviation "$GABA_A$" refers to a type A gamma-aminobutyric acid receptor, which is used interchangeably herein with the term "GABA type A receptor."

The term "subject" is meant to include any mammal, e.g., primate or human. In specific examples disclosed herein, the subject is a human. The subject in any of the methods described herein may be of any age. For instance, a human subject may be an adult. The subject can, for example, be a child (e.g., a neonate, infant, young child, adolescent). In some embodiments, the subject is in the mid-to-late teens or early twenties.

Reference will now be made in detail to specific aspects of the disclosed materials, compounds, compositions, articles, and methods, examples of which are illustrated in the accompanying Examples and Figures.

$GABA_A$ Receptor Antagonists or Inverse Agonists

Figure 4A:
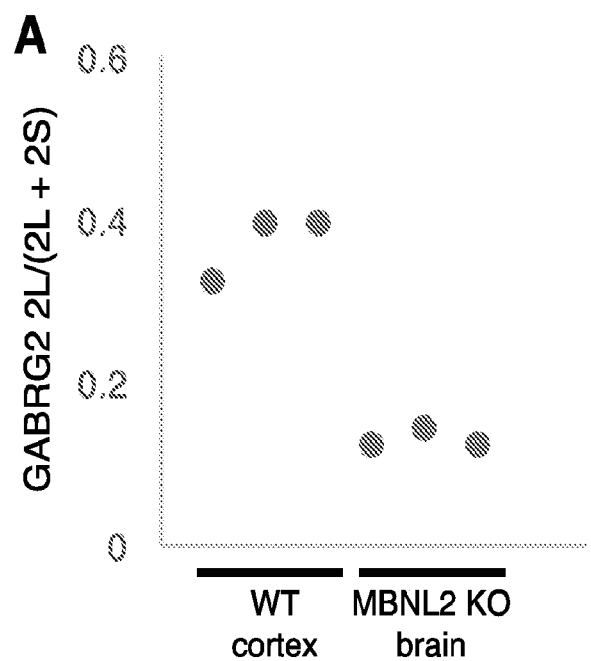
FIGS. 4A-4C are graphs showing GABRG2 mis-splicing in mouse models of DM and human DM1 post-mortem cortex.
Figure 4B:
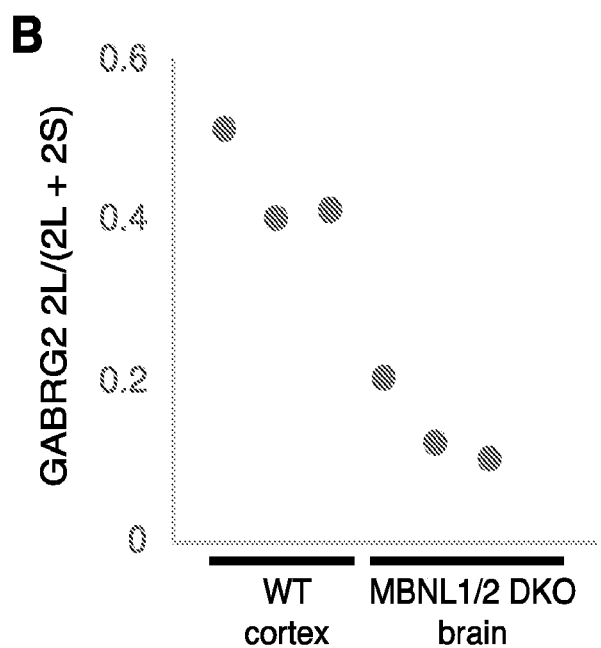
Figure 4C:
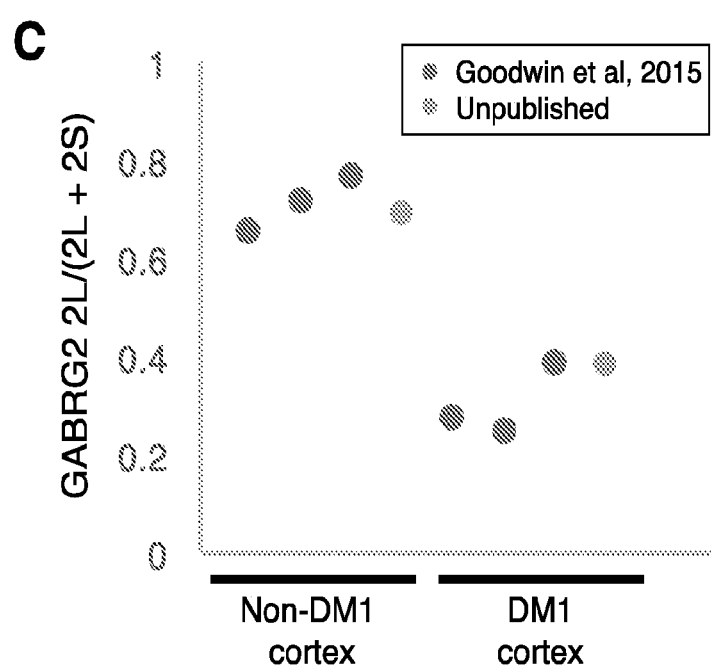

The gamma 2 subunit of the $GABA_A$ receptor (GABRG2) is mis-spliced in subjects with myotonic dystrophy, such that the ratio of mRNAs encoding gamma 2L/2S subunit isoforms comprising the obligate pentameric $GABA_A$ receptor is decreased compared to subjects unaffected by myotonic dystrophy type 1 (FIGS. 4A, 4B and 4C). GABRG2 mis-splicing in myotonic dystrophy may likely contribute to CNS dysfunction (such as hypersomnia) and other cognitive impairments in subjects with myotonic dystrophy. For example, mice expressing the gamma 2S isoform subunit of GABRG2 exclusively exhibit greater sleep times when treated with benzodiazepines as compared to those expressing normal ratios of 2L and 2S isoforms and show increased anxiety in the elevated plus maze. Additionally, endozepine-like molecules are present in the cerebrospinal fluid (CSF) of subjects with myotonic dystrophy type 1. The $GABA_A$ receptor has been shown to be hypersensitive to this endozepine(s)-like activity in patients with myotonic dystrophy.

Compounds and compositions for treating a CNS dysfunction and/or cognitive impairment associated with myotonic dystrophy in a subject are disclosed herein. The compounds and compositions disclosed herein can include a $GABA_A$ receptor antagonist or inverse agonist. In some embodiments, the $GABA_A$ receptor antagonist can be an orthosteric antagonist of the $GABA_A$ receptor. In some embodiments, the $GABA_A$ receptor antagonist can be a competitive antagonist of the $GABA_A$ receptor, such as a competitive antagonist of the benzodiazepine binding site of $GABA_A$ receptors. In other examples, the $GABA_A$ receptor antagonist can be a non-competitive antagonist of the $GABA_A$ receptor. In still other examples, the $GABA_A$ receptor antagonist can be an inverse agonist of the $GABA_A$ receptor. In further examples, the $GABA_A$ receptor antagonist can be a negative allosteric modulator of the $GABA_A$ receptor. In still further examples, the $GABA_A$ receptor antagonist can be a molecule that inhibits benzodiazepine binding protein. In some embodiments, the $GABA_A$ receptor antagonist can be a molecule that inhibit endozepine-like molecules.

In some embodiments, the $GABA_A$ receptor antagonist can be a channel blocker of the $GABA_A$ receptor.

Representative examples of $GABA_A$ receptor antagonists or inverse agonists for use herein can include, flumazenil, clarithromycin, a fluoroquinolone, picrotoxin, bicuculline, gabazine, cicutoxin, oenanthotoxin, or combinations thereof. In some embodiments, the $GABA_A$ receptor antagonist or inverse agonist is flumazenil. In other embodiments, the $GABA_A$ receptor antagonist or inverse agonist is clarithromycin. In still other embodiments, the $GABA_A$ receptor antagonist or inverse agonist is a fluoroquinolone such as ciprofloxacin. In still other embodiments, the $GABA_A$ receptor antagonist or inverse agonist is pentylenetetrazol (PTZ), Ro15-4513, sarmazenil, amentoflavone, or zinc, among other GABA type A receptor antagonists or inverse agonists known to those skilled in the art.

In some embodiments, the $GABA_A$ receptor antagonist or inverse agonist is pentylenetetrazol (PTZ). Derivatives of PTZ, such as those disclosed in WO2012/151343 can also be used.

Further examples of $GABA_A$ receptor antagonists, for use in the methods described herein, have greater affinity and/or efficacy for the $\alpha 5$ subtype than for the $\alpha 1$, $\alpha 2$ or $\alpha 3$ subtypes; these include but are not limited to Ro 15-4513, L-655,708, RY-080 (Skolnick et al., 1997 *J. Pharmacol. Exp. Ther.* 283:488-93), PWZ-029 (8-chloro-3-methoxymethyl)-5-methyl-4H-imidazo[1,5-a][1,4]benzodiazepin-6-one), RO4938581 (Ballard et al., 2009 *Psychopharmacology* 202:207-23), α5IA (3-(5-methylisoxazol-3-yl)-6-[(1-methyl-1H-1,2,3-triazol-4-yl)methoxy][1,2,4]triazolo[3,4-a]phthalazine), NGD 97-1 (CP-457,920; Bednar et al., 2004 *Clin. Pharmacol. Ther.* 75:P30), MRK-536 (Chambers et al., 2002 *J. Med. Chem.* 45:1176-79; Chambers et al., 2003 *Med. Chem.* 46:2227-40; Atack et al., 2011 *Curr. Top. Med. Chem.* 11(9):1203-14), MRK-016 (Chambers et al., 2004 *J. Med. Chem.* 47:5829-32), RY-023, S-8510 ([2-(3-isoxazolyl)-3,6,7,9-tetrahydroimidazo [4,5-d] pyrano [4,3-b] pyridine monophosphate monohydrate), RY-80, AC-3933 (5-(3-methoxyphenyl)-3-(5-methyl-1,2,4-oxadiazol-3-yl)-2-oxo-1,2-dihydro-1,6-naphthyridine), certain benzothiophene derivatives (Chambers et al., 2003 *J. Med. Chem.* 46 (11): 2227-40), certain triazolophthalazine derivatives (Sternfeld et al., 2004 *J. Med. Chem.* 47(9):2176-9; Street et al., 2004 *J. Med. Chem.* 47(14):3642-57), certain pyrazolotriazine derivatives (Chambers et al., 2004 *J. Med. Chem.* 47(24): 5829-32), and RG1662.

Formulations

In some embodiments, the $GABA_A$ receptor antagonists or inverse agonists is administered in a form of a pharmaceutical composition comprising a single active agent, wherein the $GABA_A$ receptor antagonist or inverse agonist is the single active agent, and a carrier, a diluent and/or one or more excipients.

The $GABA_A$ receptor antagonists or inverse agonists (such as flumazenil; clarithromycin; a fluoroquinolone; picrotoxin; bicuculline; gabazine; cicutoxin; oenanthotoxin, pentylenetetrazol (PTZ), Ro15-4513; sarmazenil; amentoflavone; and zinc) can be formulated for I.V., transdermal, transmucosal, sublingual, oral, and subdermal administration for use with the methods described herein. A transmucosal formulation can include sublingual, supralingual, and buccal administration. For transmucosal administration, the antagonist or inverse agonist can be combined with one or more inactive ingredients for the preparation of a tablet, packed powder, edible film strip, soft gel capsule, hard gel capsule, lozenge, or troches. For example, in some embodiments, the antagonists or inverse agonists such as flumazenil may be combined with at least one excipient such as fillers, binders, humectants, disintegrating agents, solution retarders, absorption accelerators, wetting agents absorbents, or lubricating agents. According to some embodiments, the antagonist or inverse agonist may be combined with one or more of a polyol (e.g., lactose, sucrose, mannitol, or mixtures thereof), an alcohol (e.g., ethanol), and a gum (e.g., acacia and guar), and then formed into a lozenge by conventional methods.

In some embodiments, the formulation can be a hard, compressed, rapidly dissolving tablet adapted for direct sublingual dosing. The tablet includes particles made of the antagonist or inverse agonist and a protective material. In some embodiments, these particles are provided in an amount of between about 0.01 and about 75% by weight based on the weight of the tablet (e.g., 1%, 5%, 10%, 15%, 20%, 25%, 30%, 35%, 45%, 50%, 60%, 70%, and 75%). In some embodiments, the tablet may also include a matrix made from a nondirect compression filler, a wicking agent, and a hydrophobic lubricant. In some embodiments, the tablet is adapted to dissolve spontaneously in the mouth of a patient in less than about 60 seconds (and, in some cases, in less than about 30 seconds).

In some embodiments, the formulation can be a compressed rapidly dissolving tablet comprising effervescent agents. These effervescent agents allow enhanced adsorption of the antagonist or inverse agonist across the mucosal membranes (e.g., tongue, cheek, and gums) in the oral cavity. An example of effervescent pharmaceutical compositions suitable for use in conjunction with the methods described herein are the compositions described in U.S. Pat. No. 6,200,604.

In some embodiments, the $GABA_A$ receptor antagonists or inverse agonists can be administered transmucosally using an edible film. Such films can include a carrier comprising water-soluble polymers in combination with certain ingredients and provides a therapeutic effect. In some embodiments, the film is coated and dried utilizing existing coating technology and exhibits instant wettability followed by rapid dissolution/disintegration upon administration in the oral cavity. In some embodiments, an edible film can contain as the essential components a water-soluble polymer or a combination of water-soluble polymers, one or more plasticizers or surfactants, one or more polyalcohols, and flumazenil. Non-limiting examples of edible films can be found in U.S. Pat. Nos. 5,948,430; 6,177,096; 6,284,264; 6,592,887; and 6,709,671.

Further examples of additional pharmaceutical compositions suitable for transmucosal administration include those described in U.S. Pat. Nos. 5,178,878; 5,223,264; and 6,024,981.

In some embodiments, the $GABA_A$ receptor antagonists or inverse agonists can be combined with inactive ingredients. Such ingredients may be necessary, for example, to add bulk to the pharmaceutical preparation, to bind the preparation, to add color or flavor to the preparation, and to prevent degradation or growth of contaminants.

In some embodiments, administration of the $GABA_A$ receptor antagonists or inverse agonists may be performed using an implantable device, for example, an implantable, self-regulating mechanochemical subdermal pump. In some embodiments, the device may administer the antagonist or inverse agonist on a set dosage program. In some embodiments, the device may administer the antagonist or inverse agonist on demand as determined by the subject. In some embodiments, the device may administer the antagonist or inverse agonist on a constant release profile. In some embodiments, the device may administer the antagonist or inverse agonist automatically. These devices are known in the art for the treatment of other disorders, for example, diabetes. Non-limiting examples of various embodiments of this mode of administration are detailed in U.S. Pat. Nos. 5,062,841; 5,324,518; and 6,852,104.

In some embodiments, a transmucosal administration of a $GABA_A$ receptor antagonists or inverse agonists can be combined with transdermal administration of the same or another antagonist or inverse agonist. Without being bound by theory, such a delivery mechanism may be useful for nocturnal application to assist the subject with morning wakefulness.

Transdermal administration of the $GABA_A$ receptor antagonists or inverse agonists can be accomplished by mixing the antagonist or inverse agonist with suitable pharmaceutical carriers, preservatives, optional penetration enhancers, and optional gelling agents to form ointments, emulsions, lotions, solutions, creams, gels, patches or the like, wherein a fixed amount of the preparation is applied onto a certain area of skin.

By the term "suitable pharmaceutical carrier" is meant a non-toxic pharmaceutically acceptable vehicle including, for example, polyethylene glycol, propylene glycol, isopropanol, ethanol, oleic acid, N-methylpyrrolidone, sesame oil, olive oil, wood alcohol ointments, vaseline, and paraffin or a mixture thereof.

Suitable penetration enhancers include, for example, saturated and unsaturated fatty acids and their esters, alcohols, monoglycerides, diethanolamines, N,N-dimethylamines such as linolenic acid, linolenyl alcohol, oleic acid, oleyl alcohol, stearic acid, stearyl alcohol, palmitic acid, palmityl alcohol, myristic acid, myristyl alcohol, 1-dodecanol, 2-dodecanol, lauric acid, decanol, capric acid, octanol, caprylic acid, 1-dodecylazacycloheptan-2-one sold under the trademark AZONE (Nelson Research and Development; Irvine, Calif.), ethyl caprylate, isopropyl myristate, hexamethylene lauramide, hexamethylene palmitate, capryl alcohol, decyl methyl sulfoxide, dimethyl sulfoxide, salicylic acid and its derivatives, N,N-diethyl-m-toluamide, crotamiton, 1-substituted azacycloalkan-2-ones, polyethylene glycol monolaurate and any other compounds compatible with medetomidine and its optically active enantiomers and the packages and having transdermal permeation enhancing activity.

Suitable gelling agents include, for example, hydroxy methyl cellulose, hydroxypropyl cellulose sold under the trademark KLUCEL HF (Hercules Inc.; Wilmington, Del.), tragacanth, sodium alginate, gelatin, methylcellulose, sodium carboxymethylcellulose, and polyvinyl alcohols. Suitable preservatives include, for example, parabens, benzoic acid, and chlorocresol.

Antioxidants can be included in the formulations described herein. Suitable antioxidants include, for example, ascorbyl palmirate, butylated hydroxyanisole, butylated hydroxytoluene, potassium sorbate, sodium bisulfate, sorbic acid, propyl gallate, and sodium metabisulfite.

In some embodiments, the antagonist or inverse agonist is administered by a transdermal patch. Adhesives for making transdermal patches for use in the methods described herein include polyisobutylene, silicone-based adhesives, and acrylic polymers. The adhesive polymers can be mixed with other excipients such as waxes and oils (e.g., mineral oil). A protective liner can be placed in contact with the adhesive layer to protect against drug release from the patch prior to application. Liners for use with the transdermal patches described herein include, for example, polyethylene terephthalate film, polyester membrane, and polycarbonate film.

The backing membrane of the transdermal patch for use with the methods described herein constitutes the top face surface of the transdermal patch. It may be made of a single layer or film of polymer, or be a laminate of one or more polymer layers and metal foil. Examples of polymers suitable for use in making backing films include, for example, polyester films, ethyl vinyl acetate, polypropylene, polyethylene, and polyvinyl-chloride.

In some embodiments, the administration rate of the drug is 0.1-1000 µg/h through a skin area of about 2-90 $cm^2$ (e.g., 10-30 $cm^2$). The amount of drug delivered into the skin can be controlled by a number of factors including skin patch size, degree of drug loading, the use of rate controlling membranes, permeation enhancers, and the like.

In some embodiments, the transmucosal and/or the transdermal formulation may be a time-release or slow-release formulation. In some embodiments, the transdermal formulation may be a time-release or slow-release formulation. The transmucosal or transdermal formulation described herein may also be formulated so as to provide slow or controlled release of the antagonist or inverse agonist using, for example, hydropropylmethyl cellulose in varying proportions to provide the desired release profile, other polymer matrices, gels, permeable membranes, osmotic systems, multilayer coatings, microparticles, liposomes and/or microspheres. In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

In some embodiments, the active ingredient can be in a micro-encapsulated form with one or more excipients. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

The term "slow-release" also encompasses "extended-release," "delayed-release," "sustained-release," "time-release," and the like. Suitable pharmaceutical excipients and unit dose architecture for slow release formulations may include those described in U.S. Pat. Nos. 3,062,720 and 3,247,066. Slow release formulations can be formulated in tablets that can be coated using known methods to achieve delayed disintegration in the gastrointestinal tract of a human. By way of example, a material such as glyceryl monostearate or glyceryl distearate can be used to coat tablets. Further by way of example, tablets can be coated using methods described in U.S. Pat. Nos. 4,256,108; 4,160, 452; and 4,265,874 to form osmotically-controlled release tablets. Also, the disclosed antagonist or inverse agonists can be used in its free form or as a salt and can be combined with a polymer such as polylactic-glycoloic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628), poly(ε-caprolactone) and poly(alkylene oxide) (U.S. Pub. No. 20030068384) to create a sustained release formulation.

U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566 describes the use of polymeric microparticles that release antiparasitic compositions.

The controlled-release of the active ingredient may be stimulated by various inducers, for example, pH, temperature, enzymes, water, or other physiological conditions or compounds. Various mechanisms of drug release exist. For example, in one embodiment, the controlled-release component may swell and form porous openings large enough to release the antagonist or inverse agonist after administration to a patient. The term "controlled-release component" means a compound or compounds, such as polymers, polymer matrices, gels, permeable membranes, liposomes and/or microspheres that facilitate the controlled-release of the active ingredient in the pharmaceutical composition. In another embodiment, the controlled-release component is biodegradable, induced by exposure to the aqueous environment, pH, temperature, or enzymes in the body.

The specific dose of an antagonist or inverse agonist required to obtain therapeutic benefit in the methods of treatment described herein will, usually be determined by the particular circumstances of the individual patient including the size, weight, age, and sex of the subject, the nature and stage of the disorder being treated, the aggressiveness of the disorder, and the route of administration of the compound.

For transmucosal administration (e.g., sublingual administration), for example, a daily dosage of flumazenil, for example, can range from about 0.5 mg to about 20 mg per Body Mass Index (BMI) unit (e.g., about 0.5 mg to about 15 mg; about 1 mg to about 10 mg; about 1.5 mg to about 7 mg; about 1.5 mg to about 5 mg; about 1.25 mg to about 8 mg; and about 4 mg to about 10 mg). In some embodiments, a daily dosage of flumazenil can range from about 1 mg per BMI to about 15 mg per BMI. In some embodiments, a daily dosage of flumazenil can be about 1.5 mg per BMI. In some embodiments, a daily dosage of flumazenil can be about 2 mg per BMI unit. In some embodiments, a daily dosage of flumazenil can be about 3 mg per BMI unit. For example, a subject with a BMI of 20 could be administered a daily dosage of about 40 mg of flumazenil, in other words, a daily dosage of 2 mg per BMI unit. Higher or lower doses are also contemplated, as it may be necessary to use dosages outside these ranges in some cases.

The transmucosal formulation can be administered in one single dosage or the daily dosage may be divided, such as being divided equally into two to six times per day daily dosing. In some embodiments, the transmucosal formulation is administered at least twice daily. In some embodiments, the transmucosal formulation is administered at least three times daily. In some embodiments, the transmucosal formulation is administered about every one to six hours (e.g., about every one hour; about every two hours; about every three hours; about every three and a half hours; about every four hours; about every five hours; and about every six hours). In some embodiments, the transmucosal formulation is administered by the subject as needed, e.g., patient controlled titration to a desired end effect (e.g., wakefulness or reduced sleepiness).

A transmucosal formulation may be formulated in a unit dosage form, each dosage containing from about 0.5 to about 20 mg of the antagonist or inverse agonist, e.g., flumazenil, per unit dosage (e.g., about 0.5 mg to about 15 mg; about 1 mg to about 10 mg; about 1.5 mg to about 8 mg; about 2 mg to about 7 mg; about 3 mg to about 6 mg; about 4 mg to about 8 mg; about 5 mg to about 10 mg; about 6 mg to about 12 mg; and about 8 mg to about 20 mg). In some embodiments, each dosage can contain about 5 to about 10 mg of the antagonist or inverse agonist per unit dosage. In some embodiments, each dosage contains about 6 mg of the antagonist or inverse agonist. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

For transdermal administration, for example, a daily dosage of flumazenil can range from about 0.5 mg to about 40 mg (e.g., about 2 mg to about 20 mg; about 2 mg to about 15 mg; about 1.5 mg to about 5 mg; about 2 mg to about 6 mg; about 1.25 mg to about 8 mg; and about 4 mg to about 10 mg). In some embodiments, a daily dosage of transdermal flumazenil can range from about 1 mg to about 15 mg. In some embodiments, a daily dosage of transdermal flumazenil can be about 1.5 mg. In some embodiments, a daily dosage of transdermal flumazenil can be about 2 mg. In some embodiments, a daily dosage of transdermal flumazenil can be about 3 mg. Higher or lower doses are also contemplated as it may be necessary to use dosages outside these ranges in some cases.

The transdermal formulation can be administered in one single dosage or the daily dosage may be divided, such as being divided equally into two to six times per day daily dosing. In some embodiments the transdermal formulation is formulated to a concentration of about 0.5 mg to about 20 mg per mL (e.g., about 0.5 mg to about 15 mg per mL; about 1 mg to about 10 mg per mL; about 1.5 mg to about 5 mg per mL; about 3 mg to about 7 mg per mL; about 4 mg to about 15 mg per mL; and about 4 mg to about 10 mg per mL). In some embodiments, the transdermal formulation is formulated to a concentration of about 4 mg per mL. In some embodiments, the transdermal formulation is administered once daily (e.g., before bed). In some embodiments, the transdermal formulation is administered at least twice daily. In some embodiments, the transdermal formulation is administered about every eight to about twenty-four hours (e.g., about every eight hours; about every ten hours; about every twelve hours; about every sixteen hours; about every twenty hours; about every twenty-two hours; and about every twenty-four hours). In specific embodiments, from about 5 mg to about 40 mg (e.g., about 5 mg to about 30 mg; about 5 mg to about 25 mg; about 5 mg to about 20 mg; about 6 mg to about 18 mg) can be administered every three to four hours during waking hours.

A transdermal formulation may be formulated in a unit dosage form, each dosage containing from about 0.5 to about 20 mg of flumazenil per unit dosage (e.g., about 0.5 mg to about 15 mg; about 1 mg to about 12 mg; about 1.5 mg to about 10 mg; about 2 mg to about 6 mg; about 3 mg to about 7 mg; about 4 mg to about 8 mg; and about 5 mg to about 10 mg). In some embodiments, each dosage can contain about 1 to about 15 mg of flumazenil per unit dosage. In some embodiments, each dosage contains about 2 mg of flumazenil. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The components used to formulate the pharmaceutical compositions described above are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The $GABA_A$ receptor antagonists or inverse agonists can be administered in combination with other agents. In one embodiment, the antagonist or inverse agonist is administered with an agent for treating or managing symptoms related to myotonic dystrophy. For example, the $GABA_A$ receptor antagonists or inverse agonists can be administered with an agent for treating breathing and coughing symptoms, cataracts, improving cognitive or behavioral abnormalities, treat daytime sleepiness, gastrointestinal dysfunction, wakefulness, heart abnormalities, insulin resistance, myotonic, pain, complications due to pregnancy or childbirth, skeletal muscle weakness, or a combination thereof. In certain embodiments, the $GABA_A$ receptor antagonist or inverse agonist can be administered with a stimulant. In certain embodiments, the $GABA_A$ receptor antagonist or inverse agonist can be administered with a stimulant, wherein the $GABA_A$ receptor antagonist or inverse agonist is flumazenil. In certain embodiments, the $GABA_A$ receptor antagonist or inverse agonist can be administered with a stimulant, wherein the $GABA_A$ receptor antagonist or inverse agonist is flumazenil and the stimulant is amphetamine, dextroamphetamine, dexmethylphendiate, methylphenidate, lisexamfetamine, caffeine, ephedrine, modafinil, armodafinil, or derivatives thereof. In certain embodiments, the $GABA_A$ receptor antagonist or inverse agonist can be administered with a stimulant, wherein the $GABA_A$ receptor antagonist or inverse agonist is flumazenil and the stimulant is modafinil.

The $GABA_A$ receptor antagonists or inverse agonists can be administered in an amount 1,000 mg or less per day (e.g., less than about 100 mg per day; less than about 200 mg per day; less than about 300 mg per day; less than about 400 mg per day; less than about 500 mg per day; less than about 600 mg per day). The specific dose of a $GABA_A$ receptor antagonists or inverse agonists required to obtain therapeutic benefit in the methods of treatment described herein will usually be determined by the particular circumstances of the individual subject including the size, weight, age, and sex of the subject, the nature and stage of the disorder being treated, the aggressiveness of the disorder, and the route of administration of the compound. In some embodiments, the $GABA_A$ receptor antagonists or inverse agonists can be administered once daily. In some embodiments, the $GABA_A$ receptor antagonists or inverse agonists can be administered twice daily. In some embodiments, the $GABA_A$ receptor antagonists or inverse agonists can be administered in an amount of 5 mg or greater per BMI unit. In some embodiments, the $GABA_A$ receptor antagonists or inverse agonists can be administered in an amount of 100 mg or greater per dose. For example, flumazenil can be administered in an amount of from 2 mg to 50 mg daily, from 2 mg to 40 mg daily or from 10 mg to 40 mg. Clarithromycin can be administered in an amount of from 600 to 1,000 mg daily, from 800 to 1,000 mg daily, from 600 to 3,000 mg daily or from 800 to 3,000 mg daily (e.g., 1 g or 1.5 g twice daily). In some embodiments, the subject exhibits resistance to a $GABA_A$ receptor antagonists or inverse agonists prior to administration of the antagonist or inverse agonist. In some embodiments, administration of the antagonist or inverse agonist can reverse or decrease a subject's resistance to a wakefulness promoting agent.

In some embodiments, treatment of a disorder associated with myotonic dystrophy can include the following: a) transmucosal, e.g., sublingual, administration of an antagonist or inverse agonist, e.g., flumazenil; and b) administration of an agent for treating or managing symptoms related to myotonic dystrophy.

In some embodiments, the treatment can further include: c) transdermal administration of an antagonist or inverse agonist, e.g., flumazenil.

For example, in some embodiments, a sublingual or transdermal formulation of flumazenil is administered about every 1.5 to 4 hours during the waking hours of the day (e.g., every about 3 to 3.5 hours). In some embodiments, the $GABA_A$ receptor antagonists or inverse agonists is administered from one to three times during the waking hours of the day (e.g., about every 4 hours). In some embodiments, a transdermal or time-release formulation of flumazenil is administered once daily (e.g., before bed). In some embodiments, an oral or time-release formulation of flumazenil is administered once daily (e.g., immediately upon waking). In some embodiments, a transmucosal or time-release formulation of flumazenil is administered once daily (e.g., immediately upon waking).

Methods

Provided herein are methods of treating a condition (including a dysfunction, a disease, a disorder, or an impairment) associated with myotonic dystrophy in a subject comprising administering to the subject an effective amount of a $GABA_A$ receptor antagonist or inverse agonist. The methods disclosed herein are related to myotonic dystrophy types I and II, including congenital myotonic dystrophy and forms of dystrophy with varying ages of onset. According to the Myotonic Dystrophy Foundation, manifestations of myotonic dystrophy can include dysfunction, disease, disorder, or impairment of the skeletal muscle, heart, central nervous system, smooth muscle, respiratory system, hormonal system, immune system, vision, reproductive system, or skin.

In some aspects, methods of treating a central nervous system (CNS) dysfunction associated with myotonic dystrophy in the subject are provided herein. The term "CNS dysfunction" as used herein refers to the result of a myotonic dystrophy process that is characterized by destruction of, or harm to, cells of the brain or the spinal cord, such that the normal motor and sensory control function of the brain or spinal cord is disrupted. The CNS dysfunction can be neurofunctional, neurodevelopmental, and/or neurodegenerative. Specific examples of CNS dysfunction due to myotonic dystrophy can include cognitive impairment, behavioral, emotional, and socialization difficulties, unintended sleep, excessive sleepiness, and peripheral neuropathy. The compounds and compositions disclosed herein are useful in the treatment of several dysfunctions of the CNS associated with myotonic dystrophy.

Various test methods exist for evaluating a CNS dysfunction associated with myotonic dystrophy in a subject. Particularly, the degree of excessive sleepiness (such as hypersomnia) can be evaluated by sleepiness scales (a subset of the Stanford Sleepiness Scale has been validated in myotonic dystrophy). Other test methods can include a Polysomnogram test; a Multiple Sleep Latency Test (MSLT); a Maintenance of Wakefulness Test (MWT); and psychomotor vigilance test (PVT). Additionally, overall function in myotonic dystrophy subjects can be measured by the Myotonic Dystrophy Health Index (Heatwole C. et al., *Muscle Nerve.* 2014; 49(6):906-14).

In specific embodiments, methods of treating excessive sleepiness, central and obstructive sleep apneas, restless legs syndrome (RLS), periodic leg movements in wake (PLMW) and periodic leg movements in sleep (PLMS), or nocturnal and diurnal rapid eye movement (REM) sleep dysregulation associated with myotonic dystrophy in a subject comprising administering to the subject an effective amount of a $GABA_A$ receptor antagonist or inverse agonist are provided. In particular, the methods can increase regularity of sleep rhythms in a subject; promoting wakefulness in a subject; and restoring a normal sleep pattern. In other specific embodiments, methods of treating hypersomnia associated with myotonic dystrophy in a subject, comprising administering to the subject an effective amount of a $GABA_A$ receptor antagonist or inverse agonist are provided. The term "hypersomnia" as used herein refers to a condition in which the number of hours devoted to sleeping in a 24 hour day exceed the $95^{th}$ percentile normative data for the population (i.e., generally greater than or equal to 11 hours), including an aggregate of nighttime and daytime sleep. In other specific embodiments, methods of treating hypersomnolence associated with myotonic dystrophy in a subject, comprising administering to the subject an effective amount of a $GABA_A$ receptor antagonist or inverse agonist are provided. The term "hypersomnolence" as used herein refers to a tendency to exhibit "sleepiness" or inability to remain awake during the daytime/light hours. Sleep related disorders can be characterized using various objective and subjective tests known in the art. For example, the multiple sleep latency test (MLST), maintenance of wakefulness test (MWT), Epworth Sleepiness Scale, the Stanford Sleepiness Scale, the Pittsburgh Sleep Quality Index, an Activity-Rest and Symptom Diary, Actigraphy, Psychomotor Vigilance Task (PVT), Polysomnography, Functional Magnetic Resonance Imaging, Profile of Mood States, Functional Outcomes of Sleep Questionnaire, Medical Outcomes Study Short-Form 36, electroencephalograph (EEG), and Neurophysical Testing such as the Cambridge Neurophysical Test Automated Battery (CANTAB) (e.g., physcomotor speed, attention, working memory, and executive function) can be used individually or in combination. Hypersomnia can be assessed by measures that define total amount of time/hours devoted to sleep/24 hours clock as determined by surrogate, that is, movement vs. non-movement as revealed by "actigraphy" or by numerous personal health devices (e.g., Fit-Bit™; JawBone™). Daytime sleepiness (or hypersomnolence) can be assessed by MSLT or MWT testing. In specific embodiments, methods of treating anhedonia associated with myotonic dystrophy in a subject, comprising administering to the subject an effective amount of a $GABA_A$ receptor antagonist or inverse agonist are provided. Anhedonia refers to the loss of feeling of pleasure in acts that normally give pleasure. Anhedonia can be assessed using self-rated questionnaires such as the physical anhedonia scale (PAS) and the social anhedonia scale (SAS). See for example, Chapman L. J. et al., Scales for physical and social anhedonia. *J. Abnorm. Psychol.* 1976, 85:374-382.

In certain examples disclosed herein, the hypersomnia is not stupor, shift work sleeping disorder, Parkinson's disease, obstructive sleep apnea, rapid-eye movement (REM)-sleep behavior disorder (i.e., RBD), Klein-Levin syndrome (KLS), amphetamine resistant hypersomnia, idiopathic hypersomnia, or narcolepsy, whether it be narcolepsy with cataplexy, or narcolepsy without cataplexy.

In specific embodiments, methods of treating a cognitive impairment associated with myotonic dystrophy in a subject are provided. As used herein, "cognitive" refers to the mental process of comprehension, judgment, memory, and reasoning, as contrasted with emotional and volitional processes. See for example, Mosby's Medical Dictionary, $5^{th}$ edition (1998). "Cognitive function" refers to an intellectual process by which one becomes aware of, perceives, or comprehends ideas. It involves all aspects of perception, thinking, reasoning, and remembering. As used herein, "cognitive dysfunction" or "cognitive impairment" refers to an abnormal or defective cognitive function associated with myotonic dystrophy. Typical cognitive impairments associated with myotonic dystrophy includes IQ, executive function, visual-spatial construction, arithmetic ability, attention, and personality to variable degrees. Various test methods exist for evaluating cognitive impairment in a subject. The test methods can include neuropsychological assessment which can include cognitive skills tests, age appropriate IQ tests, executive function and higher cognition skills tests, visual-spatial ordering skills, attention skills tests, verbal abstract reasoning skills tests, and temporal-sequential ordering skills tests.

In specific embodiments, methods of treating impaired cognitive and executive function, reduced alertness, reduced motivation, reduced arousal, apathy, or fatigue in a subject, comprising administering to the subject an effective amount of a $GABA_A$ receptor antagonist or inverse agonist are provided. In some embodiments, the methods can enhance/improve/promote cognitive function, cognitive performance, coherent cognitive processes, wakefulness, and/or alertness in subjects with myotonic dystrophy. In some embodiments, the methods provided herein can improve the quality of psychosocial life and relationships in a subject are provided.

As described herein, the methods for treating a condition associated with myotonic dystrophy include administering a therapeutically effective amount of a $GABA_A$ receptor antagonist or inverse agonist to the subject in need. Any suitable $GABA_A$ receptor described herein can be used including flumazenil; clarithromycin; a fluoroquinolone; picrotoxin; bicuculline; gabazine; cicutoxin; and oenanthotoxin. Flumazenil competes with endozepine-like molecules that bind to the benzodiazepine binding site on $GABA_A$ receptors. Without wishing to be bound by theory, it is believed that the benefits from flumazenil may be via two distinct but connected mechanisms—lessening downstream effects of the hypersensitive $GABA_A$ receptor (caused by GABRG2 mis-splicing), and antagonizing the endozepine(s)-like activity from binding to the benzodiazepine binding site.

In further embodiments, the subject having myotonic dystrophy to be treated can be identified by having one or more of the following criteria:

(a) The subject has daily periods of irrepressible need to sleep or daytime lapses into sleep occurring for at least three months.

(b) Cataplexy is absent.

(c) When tested on the Multiple Sleep Latency Test (MSLT) according to standard techniques, it is shown that the subject shows fewer than two sleep onset REM periods or no sleep onset REM periods if the REM latency on the preceding polysomnogram was less than or equal to 15 minutes.

(d) The presence of at least one of the following:
  1. The MSLT shows a mean sleep latency of less than or equal to 8 minutes.
  2. Total 24-hour sleep time is greater or equal to 600 minutes on 24-hour polysomnographic monitoring (performed after correction for potential chronic or acute sleep deprivation), or by wrist actigraphy in association with a sleep log (averaged over at least seven days with unrestricted sleep).

In certain embodiments, the subject to be treated will show by wrist actigraphy a total 24-hour sleep time of greater or equal to 9 hours, 10 hours, 11 hours, 12 hours, 13 hours, 14 hours, 15 hours, 16 hours or 17 hours. In some embodiments the subject is identified by having a 24-hour sleep time of 12-14 hours.

Wrist actigraphy can be performed, for instance, using a device worn on the subject's wrist. Such devices are commercially available (e.g., ACTIWATCH SPECTRUM PRO (PHILIPS, Bend, Oreg.)).

In certain embodiments, the subject to be treated will show a mean sleep latency of less than or equal to 8 minutes on an MSLT.

In certain embodiments, the subject to be treated will show a total 24-hour sleep time greater or equal to 600 minutes, greater or equal to 660 minutes, greater or equal to 720 minutes, greater or equal to 780 minutes, greater or equal to 840 minutes, greater or equal to 900 minutes, greater or equal to 960 minutes on 24-hour polysomnographic monitoring (performed after correction of chronic sleep deprivation), or by wrist actigraphy in association with a sleep log (averaged over at least seven days with unrestricted sleep).

In some embodiments, the subject to be treated will show a nocturnal sleep of 8 hours or more, 9 hours or more, 10 hours or more, 11 hours or more, 12 hours or more, 13 hours or more, or 14 hours or more, over a 24 hour period. The nocturnal sleep can be determined, for instance, by 24-hour polysomnographic monitoring (performed after correction of chronic sleep deprivation), or by wrist actigraphy in association with a sleep log (averaged over several days, e.g., at least seven days).

In certain embodiments, the subject to be treated will show by wrist actigraphy a total 24-hour sleep time of greater or equal to 9 hours, 10 hours, 11 hours, 12 hours, 13 hours, 14 hours, 15 hours, 16 hours or 17 hours. In some embodiments the subject is identified by having a 24-hour sleep time of 12-14 hours.

In some embodiments, the subject to be treated will be identified by having a score of above 10 on the Epworth Sleepiness Scale (ESS). The ESS is scale that measures daytime sleepiness by having a subject rate his or her probability of falling asleep on a scale of increasing probability from 0 to 3 for eight different situations that most people engage during their daily lives, though not necessarily every day. A score below 10 is considered normal. A number of the ESS in the 10-24 range indicates is predictive of the subject having a sleep disorder.

In certain embodiments, the symptom of myotonic dystrophy to be treated is mental fog. Mental fog can, for example, be identified in a subject that reports a subjective experience of, for instance, inattention, such as an inability to attend to daily tasks, thought process abnormalities, inability to think clearly, automatic behaviors (e.g., almost robotic recitation of behaviors that are incongruent with the situation or physical/temporal environment), comprehension abnormalities and/or language abnormalities. The subject may, for example, report a sensation of mental clouding that would be described as feeling "foggy."

The subject can for instance be identified as having a symptom (e.g., hypersomnia, excessive daytime sleepiness or mental fog) of myotonic dystrophy in the absence of sleep apnea, or increased respiratory effort related arousal.

A determination of whether the treatment is useful in performing the methods described herein can be made using known methods in the art. For example, a determination of whether the treatment is useful can include direct observation of behavioral or physiological properties of mammalian sleep, by self-reporting, electromyography, genetic testing, and/or by various other well-known methods described herein, including electrophysiological methods. Electromyography measures the action potentials produced by muscles, and is therefore useful for diagnosing diseases that primarily affect muscle function, including the muscular dystrophies such as myotonic dystrophy. Electromyography is performed with a standard electromyograph and concentric needle electrodes. The doctor inserts electrodes into a muscle which records action potentials that occur when the muscle is at rest and during voluntary contractions directed by the doctor. Pfeilsticker et al., *Arq Neuropsiquiatr,* 2001, 59:186-191. Genetic testing can identify a human as having myotonic dystrophy. Because DM1 results from CTG repeat expansion in the DMPK gene on chromosome 19q13.3. and DM2 results from CCTG repeat expansion in the ZNF9 gene located on chromosome 3q21.3, genetic testing can be done on a blood or tissue sample. See, e.g., Liguori et al., *Science,* 2001, 293(5531):864-867. Genetic tests for myotonic dystrophy are known to those skilled in the art. Numerous academic, institutional and for-profit laboratories offer genetic testing services.

Another object of the present disclosure is the use of a compound as described herein (e.g., of any formulae herein) in the manufacture of a medicament for use in the treatment of a disorder or disease delineated herein. Another object of the present disclosure is the use of a compound as described herein (e.g., of any formulae herein) for use in the treatment of a disorder or disease delineated herein. Another object of the present disclosure is the use of a compound as described herein (e.g., of any formulae herein) in the manufacture of topical composition for use in the treatment or prevention of a disorder or disease delineated herein.

In some embodiments, the $GABA_A$ receptor antagonist or inverse agonist is administered at least once daily for at least five consecutive days. The $GABA_A$ receptor antagonist or inverse agonist can, for example, be administered at least once a day, twice a day, three times a day or four times a day. Doses of the $GABA_A$ receptor antagonist or inverse agonist can, for example, be administered at a dose of about 1 mg to 1,000 mg, about 1 mg to 800 mg, or about 1 mg to 600 mg per day. In certain examples, administration can be oral, transdermal, or I.V.

In some embodiments, the $GABA_A$ receptor antagonist or inverse agonist is administered at least once daily for at least five consecutive days; or wherein the $GABA_A$ receptor antagonist or inverse agonist is to be administered at least once a day, twice a day, three times a day or four times a day; or wherein the $GABA_A$ receptor antagonist or inverse agonist is to be administered at a dose of about 1 mg to 1,000 mg, about 1 mg to 800 mg, or about 1 mg to 600 mg; or wherein the $GABA_A$ receptor antagonist or inverse agonist is administered orally; or wherein the $GABA_A$ receptor antagonist or inverse agonist is flumazenil, and the flumazenil is to be administered to the subject in lozenges taken every 1.5 to 4.0 hours during the subject's waking hours; and/or in transdermal patches; such that about 55 mg to about 100 mg flumazenil is administered to the subject per day.

In some embodiments, a single dose of the $GABA_A$ receptor antagonist or inverse agonist is administered to the subject at one time. In other embodiments, multiple doses of the $GABA_A$ receptor antagonist or inverse agonist are given to the subject over a period of time (e.g., over a period of hours, days, weeks, months, or even years). For certain routes of administration (e.g., transdermal), administration is continuous.

In some embodiments, the method comprises the step of administering the $GABA_A$ receptor antagonist or inverse agonist to the subject at a dose of between 0.005 mg/kg and 25 mg/kg, between 0.01 mg/kg and 10 mg/kg, between 0.001 mg/kg and 0.2 mg/kg, between 0.01 mg/kg and 2 mg/kg, between 0.03 mg/kg and 6 mg/kg, or between 0.05 mg/kg and 0.5 mg/kg.

In some embodiments, the method comprises the step of administering the $GABA_A$ receptor antagonist or inverse agonist to the subject at a dose of about 25 mg/kg of patient weight, about 20 mg/kg, about 10 mg/kg, about 5 mg/kg, about 3 mg/kg, about 1 mg/kg, about 0.3 mg/kg, about 0.1 mg/kg, about 0.05 mg/kg, about 0.025 mg/kg, or about 0.01 mg/kg.

In some embodiments, the method comprises the step of administering the $GABA_A$ receptor antagonist or inverse agonist to the subject at a daily dose of from 0.05 mg/day to 100 mg/day, 1 mg/day to 90 mg/day, 5 mg/day to 85 mg/day, 0.1 mg/day to 5 g/day, from 1 mg/day to 1 g/day, or from 3 mg/day to 300 mg/day. In various embodiments, the administered dose is about 1.25 g, about 1 g, about 750 mg, about 500 mg, about 250 mg, about 200 mg, about 100 mg, about 50 mg, about 25 mg, about 10 mg, about 5 mg, about 1 mg, about 0.5 mg, about 0.25 mg, or about 0.05 mg.

In some embodiments, the method comprises the step of administering the $GABA_A$ receptor antagonist or inverse agonist to the subject at a dose of about 1 mg to 1.25 g, about 5 mg to 1 g, about 10 to 800 mg, about 25 mg to 600 mg, about 50 mg to 400 mg, or about 100 mg to 200 mg. In some embodiments, the method comprises the step of administering the $GABA_A$ receptor antagonist or inverse agonist to the subject at a dose of about 1.25 gm, about 1 gm, about 750 mg, about 500 mg, about 250 mg, about 200 mg, about 100 mg, about 50 mg, about 25 mg, about 10 mg, about 5 mg, about 1 mg, about 0.5 mg, about 0.25 mg, or about 0.05 mg.

In some embodiments, the dose of the $GABA_A$ receptor antagonist or inverse agonist is administered as a unit dose (e.g., in a tablet, capsule, ampule or other form). In some embodiments, the dose of the $GABA_A$ receptor antagonist or inverse agonist is administered in an implantable device. In various embodiments, the dose of the $GABA_A$ receptor antagonist or inverse agonist is released from the implantable device over a period of time. In certain embodiments, the period of time is more than 6 hours, 12 hours, 24 hours, 2 days, 3 days, 5 days, 1 week, two weeks or one month.

In certain embodiments, flumazenil is administered to the subject transdermally, in amounts of 9 mg up 18 mg every 3.5-4.0 waking hours. In some embodiments, the flumazenil is administered transdermally. In other embodiments it is administered transdermally together with an oral formulation. An oral formulation can, for instance, be in a tablet, capsule, ampule, lozenge form, among other forms, and can contain about 0.25 mg, about 1 mg, about 2 mg, about 3 mg, about 4 mg, about 5 mg, about 6 mg, about 7 mg, about 8 mg, about 9 mg or about 10 mg flumazenil. Flumazenil can be administered every 90-120 minutes during waking hours. Flumazenil may be administered in amounts of about 55 mg-100 mg per day, or 60 mg-80 mg per day.

In some embodiments, the $GABA_A$ receptor antagonist or inverse agonist is administer at a dosage about 1 mg to about 600 mg, or 1 mg to about 800 mg, or 1 mg to about 1,000 mg.

In some embodiment, the $GABA_A$ receptor antagonist or inverse agonist is administered subcutaneously, intramuscularly, intraperitoneally, intracranially, intravenously, orally. In certain embodiments, the $GABA_A$ receptor antagonist or inverse agonist is administered orally.

In some embodiments, the $GABA_A$ receptor antagonist or inverse agonist is administered at least once a day, twice a day, three times a day or four times a day. In some embodiments, the $GABA_A$ receptor antagonist or inverse agonist is administered in a single daily dose, or the total daily dose may be administered in divided doses, two, three, or more times per day.

In some embodiments, the $GABA_A$ receptor antagonist or inverse agonist is administered for at least two consecutive days, at least about one week, at least about two weeks, at least about three weeks, at least about one month, or longer.

In some embodiments, the $GABA_A$ receptor antagonist or inverse agonist is administered at least once daily for at least five consecutive days. In some embodiments, the $GABA_A$ receptor antagonist or inverse agonist is administered to a subject with ongoing myotonic dystrophy.

In some embodiments, the $GABA_A$ receptor antagonist or inverse agonist is administered in one or more cycles. In certain embodiments, the cycles of $GABA_A$ receptor antagonist or inverse agonist administration are about 1 day cycles, 2 day cycles, 3 day cycles, 4 day cycles, 5 day cycles, 6 day cycles, 1 week cycles, 2 week, 4 week cycles, 6 week cycles, or 3 month cycles. Typically, the cycles of $GABA_A$ receptor antagonist or inverse agonist administration are about 1 week cycles. In some embodiments, two or more cycles of administration of the $GABA_A$ receptor antagonist or inverse agonist are separated by a drug holiday. In certain embodiments, drug holidays last about 1 day, 2 days, 3 days, 4 days, 5 days, 6 days, 1 week, 2 weeks or 4 weeks.

In certain embodiments, the $GABA_A$ receptor antagonist or inverse agonist is administered to the subject in absence of dextroamphetamine, methylphenidate, or a wakefulness-promoting agent such as modafinil. For example, the subject being administered with the $GABA_A$ receptor antagonist or inverse agonist will not be concurrently administered with dextroamphetamine, methylphenidate, or a wakefulness-promoting agent such as modafinil during the period of time over which the $GABA_A$ receptor antagonist or inverse agonist is administered to the subject.

Assays

Provided herein are also methods of diagnosing and treating a patient suffering from myotonic dystrophy associated with the endogenous production of $GABA_A$ receptor modulators, e.g., excessive production of such modulators as assessed in biological fluids obtained from an individual affected by DM1 such as urine, whole blood, fractions of whole blood (e.g., serum or plasma), cerebrospinal fluid (CSF), or dialysate collected from various tissues/organs including blood or parenchymal brain tissue. In some embodiments, the subject with myotonic dystrophy may be producing endogenous benzodiazepines (i.e. "endozepines").

A method of diagnosing a patient suffering from myotonic dystrophy associated with increased production of, for example, endozepines can be performed by measuring the effect of a subjects' cerebral spinal fluid (CSF) or blood or plasma on recombinant $GABA_AR$ function under whole cell patch clamp conditions (see, e.g., FIG. 1 and FIGS. 2A-2D). In some embodiments, the effect of the CSF or blood or plasma can be compared to the effect observed when the CSF or blood or plasma is co-applied with a $GABA_A$ receptor antagonist or inverse agonist such as flumazenil. In some embodiments, application of the antagonist or inverse agonist such as flumazenil can modulate the response of a CSF or blood sample of a subject as measured in a GABA whole cell patch clamp efficacy assay to within 25% of a control sample response. In some embodiments, the modulation is a decrease in the response of the CSF sample of the subject in the presence of the antagonist or inverse agonist such as flumazenil. In some embodiments, the effect of the CSF or blood or plasma in an assay expressing benzodiazepine sensitive receptors can be compared to the effect observed of the CSF or blood or plasma in an assay expressing benzodiazepine insensitive receptors. In some embodiments, the substance in the CSF or blood or plasma sample of a subject potentiates the response of GABA as measured in a GABA whole cell patch clamp efficacy assay. In some embodiments, the potentiation of the GABA response in the benzodiazepine sensitive receptors and the potentiation of the GABA response in the benzodiazepine insensitive receptors are within ±25% of each other. In some embodiments, the persistence of potentiation within ±25% of the GABA responses in benzodiazepine sensitive and insensitive receptor assays is indicative that the subject would benefit from treatment with a $GABA_A$ receptor antagonist or inverse agonist. In some embodiments, the $GABA_A$ receptor antagonist or inverse agonist is flumazenil.

A method of diagnosing a patient suffering from myotonic dystrophy, which can be used with any of the disclosed treatment methods, can be by electromyography and/or genetic testing.

Further, a method of diagnosing a patient suffering from $GABA_A$ mediated CNS dysfunction (such as hypersomnia) or cognitive impairment associated with increased production of, for example, endozepines can be performed by measuring the effect of a subjects' cerebral spinal fluid (CSF) or blood or plasma on recombinant $GABA_AR$ function under whole cell patch clamp conditions.

In further examples, the disclosed methods can further comprise identifying the subject as having hypersomnia or excessive daytime sleepiness wherein the subject is identified by exhibiting a mean sleep latency of less than or equal to 8 minutes on the Multiple Sleep Latency Test (MSLT); exhibiting a total 24 hour sleep time that is greater or equal to 9.5 hours determined on 24-hour polysomnographic monitoring or by wrist actigraphy in association with a sleep log averaged over 7 days with unrestricted sleep; and/or exhibiting a score above 10 on the Epworth Sleepiness Scale (ESS).

Kits

Also provided herein are kits for treating disorders associated with myotonic dystrophy. A kit can include an I.V., transdermal, oral, or transmucosal (e.g., sublingual, supralingual, and buccal) formulation of a $GABA_A$ receptor antagonist or inverse agonist. In some embodiments, the $GABA_A$ receptor antagonist or inverse agonist is flumazenil. In some embodiments, the kit can further include one or more of a wakefulness promoting agent (e.g., modafinil) and a transdermal formulation of a $GABA_A$ receptor antagonist or inverse agonist. In some embodiments, a kit can include one or more delivery systems and directions for use of the kit (e.g., instructions for treating a subject). In some embodiments, a kit can include a sublingual formulation of flumazenil and a transdermal formulation of flumazenil. In another embodiment, a kit can include a sublingual formulation of flumazenil and a wakefulness promoting agent. In some embodiments, the kit can include a sublingual formulation of flumazenil and a label that indicates that the contents are to be administered to a subject resistant to amphetamines. In another embodiment, the kit can include a sublingual formulation of a $GABA_A$ receptor antagonist or inverse agonist such as flumazenil and a label that indicates that the contents are to be administered to a subject positive for increased production of endozepines or other somnogenic compounds, as described herein. In a further embodiment, a kit can include a sublingual formulation of flumazenil and a label that indicates that the contents are to be administered with a wakefulness promoting agent and/or a transdermal formulation of flumazenil.

Also provided herein are kits for performing a diagnostic assay. In some embodiments, the diagnostic assay can be used to diagnose subjects suffering from a myotonic dystrophy and/or to determine subjects that would benefit from treatment with a $GABA_A$ receptor antagonist or inverse agonist. In some embodiments, a kit for use as a diagnostic assay is provided with the components for carrying out a patch clamp assay as described herein. In some embodiments, the kit can include a $GABA_A$ receptor antagonist or inverse agonist and cells which transiently or stably express human α1β2γ2s $GABA_A$ receptors. In some embodiments, the kit can include cells which transiently and stably express human α1β2γ2s $GABA_A$ receptors and cells which transiently and stably express a benzodiazepine insensitive subunit (e.g., α1(H102R). In some embodiments, the kit further comprises one or more of an extracellular solution that can function as a control sample, e.g., a control CSF sample; an intracellular solution; an extracellular medium, a motor-driven solution exchange device; and instructions for use of the kit.

Further Embodiments

Provided below are additional non-limiting embodiments of the disclosure.

Paragraph 1. A method for treating a symptom of myotonic dystrophy in a human comprising administering an effective amount of a GABA type A receptor antagonist or inverse agonist to the human, wherein the symptom is selected from the group consisting of hypersomnia, excessive daytime sleepiness and mental fog.

Paragraph 2. The method of paragraph 1, further comprising identifying the human as having myotonic dystrophy prior to administering the GABA type A receptor antagonist or inverse agonist to the human.

Paragraph 3. The method of paragraph 2, wherein the human is identified as having myotonic dystrophy by electromyography and/or genetic testing.

Paragraph 4. The method of any one of paragraphs 1-3, wherein the GABA type A receptor antagonist or inverse agonist is a channel blocker of the GABA type A receptor.

Paragraph 5. The method of any one of paragraphs 1-3, wherein the GABA type A receptor antagonist or inverse agonist is selected pentylenetetrazol (PTZ) or picrotoxin.

Paragraph 6. The method of any one of paragraphs 1-3, wherein the GABA type A receptor antagonist or inverse agonist is selected from the group consisting of flumazenil, Ro15-4513, sarmazenil, amentoflavone, and zinc.

Paragraph 7. The method of any one of paragraphs 1-3, wherein the GABA type A receptor antagonist or inverse agonist is PTZ.

Paragraph 8. The method of any one of paragraphs 1-7, wherein the GABA type A receptor antagonist or inverse agonist is administered in a form of a pharmaceutical composition consisting essentially of a single active agent, wherein the GABA type A receptor antagonist or inverse agonist is the single active agent, and a carrier, a diluent and/or one or more excipients.

Paragraph 9. The method of any one of paragraphs 1-8, wherein the symptom of myotonic dystrophy is hypersomnia or excessive daytime sleepiness.

Paragraph 10. The method of paragraph 9, further comprising identifying the human as having hypersomnia or excessive daytime sleepiness wherein the human is identified by exhibiting a mean sleep latency of less than or equal to 8 minutes on the Multiple Sleep Latency Test (MSLT);

exhibiting a total 24 hour sleep time that is greater or equal to 9 hours determined on 24-hour polysomnographic monitoring or by wrist actigraphy in association with a sleep log averaged over 7 days with unrestricted sleep; and/or exhibiting a score above 10 on the Epworth Sleepiness Scale (ESS).

Paragraph 11. The method of any one of paragraphs 1-10, wherein the GABA type A receptor antagonist or inverse agonist is administered at least once daily for at least five consecutive days.

Paragraph 12. The method of any one of paragraphs 1-10, wherein the GABA type A receptor antagonist or inverse agonist is administered at least once a day, twice a day, three times a day or four times a day.

Paragraph 13. The method of any one of paragraphs 1-10, wherein the GABA type A receptor antagonist or inverse agonist is administered at a dose of about 1 mg to 1,000 mg.

Paragraph 14. The method of paragraph 13, wherein the GABA type A receptor antagonist or inverse agonist is administered at a dose of about 1 mg to 800 mg.

Paragraph 15. The method of paragraph 14, wherein the GABA type A receptor antagonist or inverse agonist is administered at a dose of about 1 mg to 600 mg.

Paragraph 16. The method of any one of paragraphs 1-15, wherein the GABA type A receptor antagonist or inverse agonist is administered orally.

Paragraph 17. The method of any one of paragraphs 1-15, wherein the GABA type A receptor antagonist or inverse agonist is flumazenil, and the flumazenil is administered to the subject in lozenges taken every 1.5 to 4.0 hours during the subject's waking hours; and/or in transdermal patches;

such that about 55 mg to about 100 mg flumazenil is administered to the subject per day.

Paragraph 18. A composition comprising or consisting essentially of a GABA type A receptor antagonist or inverse agonist for treating a symptom of myotonic dystrophy in a human, wherein the symptom is selected from the group consisting of hypersomnia, excessive daytime sleepiness and mental fog.

Paragraph 19. The composition of paragraph 18, wherein the human is identified as having myotonic dystrophy prior to being administered with the GABA type A receptor antagonist or inverse agonist.

Paragraph 20. The composition of paragraph 19, wherein the human is identified as having myotonic dystrophy by electromyography and/or genetic testing.

Paragraph 21. The composition of any one of paragraphs 18-20, wherein the GABA type A receptor antagonist or inverse agonist is a channel blocker of the GABA type A receptor; or wherein the GABA type A receptor antagonist or inverse agonist is selected pentylenetetrazol (PTZ) or picrotoxin; or wherein the GABA type A receptor antagonist or inverse agonist is selected from the group consisting of flumazenil, Ro15-4513, sarmazenil, amentoflavone, and zinc; or wherein the GABA type A receptor antagonist or inverse agonist is PTZ.

Paragraph 22. The composition of any one of paragraphs 18-21, wherein the composition consists essentially of the GABA type A receptor antagonist or inverse agonist and one or more carriers, a diluent and/or one or more excipients.

Paragraph 23. The composition of any one of paragraphs 18-22, the human is identified as having hypersomnia or excessive daytime sleepiness by exhibiting a mean sleep latency of less than or equal to 8 minutes on the Multiple Sleep Latency Test (MSLT);

exhibiting a total 24 hour sleep time that is greater or equal to 9 hours determined on 24-hour polysomnographic monitoring or by wrist actigraphy in association with a sleep log averaged over 7 days with unrestricted sleep; and/or exhibiting a score above 10 on the Epworth Sleepiness Scale (ESS).

Paragraph 24. The composition of any one of paragraphs 18-23, wherein the GABA type A receptor antagonist or inverse agonist is to be administered at least once daily for at least five consecutive days; or wherein the GABA type A receptor antagonist or inverse agonist is to be administered at least once a day, twice a day, three times a day or four times a day; or wherein the GABA type A receptor antagonist or inverse agonist is to be administered at a dose of about 1 mg to 1,000 mg, about 1 mg to 800 mg, or about 1 mg to 600 mg; or wherein the GABA type A receptor antagonist or inverse agonist is administered orally;

or wherein the GABA type A receptor antagonist or inverse agonist is flumazenil, and the flumazenil is to be administered to the subject in lozenges taken every 1.5 to 4.0 hours during the subject's waking hours; and/or in transdermal patches;

such that about 55 mg to about 100 mg flumazenil is administered to the subject per day.

Paragraph 25. The composition of any one of paragraphs 18-24, wherein the composition is used in the manufacture of a medicament for treating a symptom of myotonic dystrophy in a human, wherein the symptom is selected from the group consisting of hypersomnia, excessive daytime sleepiness and mental fog.

EXAMPLES

The following examples are set forth below to illustrate the compositions, methods, and results according to the disclosed subject matter. These examples are not intended to be inclusive of all aspects of the subject matter disclosed herein, but rather to illustrate representative methods, compositions, and results. These examples are not intended to exclude equivalents and variations of the present disclosure, which are apparent to one skilled in the art.

Example 1

Use of Flumazenil or other competitive antagonists or inverse agonists, non-competitive antagonists or inverse agonists, negative allosteric modulators (NAM) or inverse agonists that inhibit GABRG2 function, endozepine-like molecules or benzodiazepine binding proteins for treatment of CNS symptoms in myotonic dystrophy (DM1, DM2), including hypersomnia, anhedonia, impaired cognition and executive function, reduced alertness, motivation and arousal.

Individuals with myotonic dystrophy (DM) experience a wide range of symptoms referable to dysfunction of the CNS including hypersomnia and cognitive impairment. GABA is a major neurotransmitter responsible for inhibitory activity within the central nervous system (CNS), and DM mouse models lacking MBNL proteins are hyper-sensitized to GABA agonists. The cerebrospinal fluid of patients with a related condition, idiopathic hypersomnia (IH), has been previously discovered to contain a benzodiazepine-like substance whose effects can be reversed by $GABA_A$ receptor antagonists or inverse agonists. Some previously studied IH patients responsive to $GABA_A$ receptor antagonists or inverse agonists were later diagnosed with DM1, suggesting an underlying shared pathology.

A subject complaining of constant daytime sleepiness and "brain fog" participated in a sleep study to measure sleep latency, REM frequency, and other parameters to characterize hypersomnia. The data showed that the subject exhibited typical symptoms of hypersomnia without sleep apnea, restless leg syndrome, etc. A skin biopsy, CSF and blood were collected. The subject was prescribed a topical and sublingual $GABA_A$ receptor antagonist or inverse agonist. A psychomotor vigilance test and neuropsychological testing were performed while on and off the treatment.

Cerebrospinal fluid of several DM1 subjects were also assayed for benzodiazepine activity using patch-clamp electrophysiological assays (a method in which human GABR genes are expressed in a HEK293 cell and the function of the expressed gene product is recorded in real time using a combination of a glass micropipette, a high-gain low-noise amplifier and a semi-automated perfusion system to apply agonists, antagonists, modulators and patient CSF to the receptors). See for example, Rye, et al., Sci. Transl. Med. 2012; 4(161):161. These patients were treated with $GABA_A$ receptor antagonists or inverse agonists and administered subjective and objective tests of wakefulness, arousal, and cognitive function. The splicing status of the γ subunit of the $GABA_A$ receptor in post-mortem DM1 brain was also studied by RNA-Seq (a method in which the transcriptome is profiled using RNA isolated from DM1 and non-DM1 post-mortem brain. Short sequence reads derived from cDNA libraries are mapped to the transcriptome, and the inclusion level of alternative exons is quantitated by methods such as MISO). See Katz, Y. et al., Nat. Methods. 2010; 7(12):1009-15.

As shown in FIG. 1, a molecule with benzodiazepine-like properties (an "endozepine-like molecule") was found in the cerebrospinal fluid (CSF) of each of four myotonic dystrophy type 1 (DM1) subjects. Previous work has shown that flumazenil, a competitive antagonist or inverse agonist of the benzodiazepine binding site of $GABA_A$ receptors, inhibits endozepine-like molecule binding and has yielded clinical benefit in idiopathic hypersomnia (IH) subjects (Rye, D. B., et al. (2012) Modulation of vigilance in the primary hypersomnias by endogenous enhancement of $GABA_A$ receptors. Sci. Transl. Med. 4, 161ra151; Trotti, L. M., et al. (2016) Flumazenil for the Treatment of Refractory Hypersomnolence: Clinical Experience with 153 Patients. J. Clin. Sleep Med. 12, 1389-1394).

In this example, one subject ultimately found by clinical criteria, EMG, and genetic testing to suffer from myotonic dystrophy subject (DM1 in Table 1) showed improved vigilance/alertness with intravenously-administered flumazenil, as well as when flumazenil was administered by topical cream and sublingual lozenge. This was evident as assessed by a marked reduction in lapses in attention (i.e., reaction times>500 ms) in the ten-minute psychomotor vigilance task, as well as a subjective perception of reduced sleepiness as assessed by the Stanford sleepiness scale, as an average of 3 individual assessments performed over one hour (10-30 and 60 minutes) following intravenous administration of 2.0 mg of flumazenil (see FIGS. 2A-2D).

TABLE 1

Treatments for hypersomnia and cognitive deficits in four subjects (DM subject 1, undiagnosed at the time, from Rye, D. B., et al. (2012) Modulation of vigilance in the primary hypersomnias by endogenous enhancement of $GABA_A$ receptors. Sci. Transl. Med. 4, 161ra151).

| DM Subject No. | Oral clarithromycin | Intravenous flumazenil | Topical and sublingual flumazenil treatment | Current wake-promoting medication |
| --- | --- | --- | --- | --- |
| 1 | discontinued use - dysgeusia and gastrointestinal side effects | 1 year | 3-4 months | dextroamphetamine |
| 2 | efficacious | — | — | — |
| 3 | — | — | — | methylphenidate |
| 4 | — | — | 5-6 weeks | flumazenil |

Figure 3:
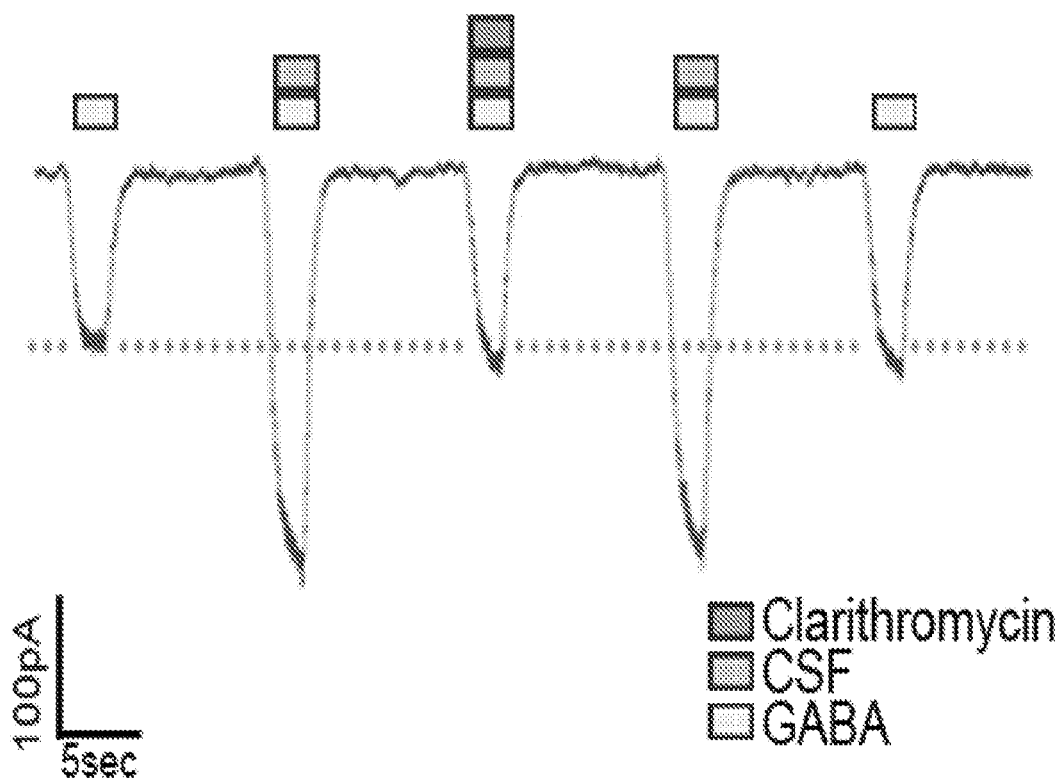
FIG. 3 is a graph showing patch clamp electrophysiology of GABRG2S-containing receptors in HEK293T cells, in the presence of GABA, CSF from DM subject 2, and/or clarithromycin. GABA, CSF from DM subject 2, and/or clarithromycin were added in combinations as indicated. The CSF exhibits endozepine-like activity that is normalized by clarithromycin.

One myotonic dystrophy subject (DM2 in Table 1) showed clinical benefit when treated with clarithromycin, also a competitive antagonist of the benzodiazepine binding site. Endozepine-like activity was demonstrated by patch clamp electrophysiology in HEK293T cells, and was reversed by addition of clarithromycin (FIG. 3).

One myotonic dystrophy subject (DM4 in Table 1) showed endozepine-like activity in their CSF and was treated with flumazenil administered transdermally via a topical cream (1 mL of a 12 mg/mL formulation), and sublingual 6 mg lozenges (2-3 lozenges per day). This subject's self-reported outcome measures before and after 6 continuous weeks of daily flumazenil use are shown in Table 2A. Another myotonic dystrophy subject was treated with flumazenil or armodafinil. This subject's self-reported outcome measures before and after flumazenil or armodafinil use are shown in Table 2B.

TABLE 2A

Subjective metrics obtained from DM subject 4, before and after flumazenil treatment. Dose of flumazenil was 12-18 mg sublingual plus 12 mg topical daily.

| Test Dependent Measure | Flumazenil OFF | Flumazenil ON | Clinically meaningful |
|---|---|---|---|
| Epworth Sleepiness Scale | 13 | 5 | Δ3-4 |
| Multidimensional Fatigue Inventory (0-100) | 66 | 47 | |
| General Fatigue (5-20) | 17 | 11 | |
| Physical Fatigue (5-20) | 10 | 11 | |
| Mental Fatigue (5-20) | 17 | 10 | |
| Reduced Activity (5-20) | 13 | 8 | |
| Reduced Motivation (5-20) | 9 | 7 | |
| Fatigue severity scale (7-63) | 57 | 38 | |
| Sleep inertia questionnaire | 73 | 41 | |
| Functional Outcomes of sleep (5-20) | 9.96 | 18.70 | Δ2-3 |
| Hypersomnia Severity Index (0-36) | 32 | 17 | |

TABLE 2B

Subjective metrics obtained from an additional DM subject, before and after flumazenil treatment or armodafmil treatment. Dose of flumazenil was 12-18 mg sublingual plus 12 mg topical daily. Dose of armodafmil was 250 mg QAM.

| Test Dependent Measure | OFF | ON Armodafmil | ON Flumazenil | Clinically meaningful |
|---|---|---|---|---|
| Epworth Sleepiness Scale | 11 | 8 | 7 | Δ3-4 |
| Multidimensional Fatigue Inventory (0-100) | | | | |
| General Fatigue (5-20) | 13 | 15 | 8 | |
| Physical Fatigue (5-20) | 8 | 6 | 5 | |
| Mental Fatigue (5-20) | 10 | 11 | 4 | |
| Reduced Activity (5-20) | 13 | 7 | 6 | |
| Reduced Motivation (5-20) | 8 | 5 | 5 | |
| Fatigue severity scale (7-63) | 54 | 47 | 24 | |
| Owl Lark | 35 | 36 | 42 | |
| Sleep inertia questionnaire | 14.9 | 14.683 | 5.775 | |
| Functional Outcomes of sleep (5-20) | 16.25 | 16.875 | 19.375 | Δ2-3 |
| Hypersomnia Severity Index (0-36) | 26 | 25 | 10 | |
| Beck Depression Inventory (0-39) | 2 | 3 | 1 | |

Dramatic improvements in hypersomnia, alertness, mental processing, and cognitive function are evident. In addition, processing speed as measured by the Symbol Digit Modalities Test showed improvement from the $21^{st}$ percentile to the $72^{nd}$ percentile, without and with flumazenil, respectively (Table 3). With flumazenil, this individual also experienced a reduction in total habitual sleep time per day, and felt that naps of equal or lesser length of time were more refreshing as compared to when not administering flumazenil. Although this individual showed dramatic improvement phenotypically, cellular assays showed that $GABA_A$ receptor potentiation induced by their CSF was not reversed by flumazenil as was reported for the CSF of other subjects complaining of hypersomnia and in whom intravenous flumazenil improved subjective and objective vigilance metrics (Rye, D. B., et al. (2012) Modulation of vigilance in the primary hypersomnias by endogenous enhancement of $GABA_A$ receptors. Sci. Transl. Med. 4, 161ra151). Moreover, DM CSF does not contain the same biomarkers as IH, therefore suggests a different underlying biology than in IH.

TABLE 3

Symbol Digit Modalities Test results from DM subject 4, with and without transdermal plus sublingual flumazenil treatment. This test measures certain aspects of processing speed. See the improvement in performance in score during administration of a combination of 12-18 mg sublingual plus 12 mg topical flumazenil daily.

| Flumazenil | T | Percentile |
|---|---|---|
| ON | 56 | 72% |
| OFF | 42 | 21% |

The mis-splicing of gamma 2 subunit of the $GABA_A$ receptor (GABRG2) exon 9 in human post-mortem DM1 brain tissue is mirrored in mouse models of DM1—models that are genetically depleted of Muscleblind-like protein expression in the brain. Mouse models genetically lacking Muscleblind-like 2 (Mbnl2) and mouse models genetically lacking both Muscleblind-like 1 (Mbnl1) and Mbnl2 were analyzed for GABRG2 mis-splicing. Mice lacking expression of Mbnl2 or both Mbnl1 and Mbnl2 in the brain were subjected to RNAseq. The transcriptomes were analyzed and the inclusion level of GABRG2 exon 9 was quantitated and compared to GABRG2 splicing data from human post-mortem DM1 brain tissue. Consistent with the observations in human DM1 post-mortem brain, GABRG2 was mis-spliced in human DM1 postmortem brain and in both the MBNL2 KO mice model of DM1 and the MBLN1/2 KO mice model of DM1, such that the ratio of mRNAs encoding gamma 2L/2S subunit isoforms comprising the obligate pentameric $GABA_A$ receptor is decreased vs. that in brains of those unaffected by DM1 and wild-type mice, FIGS.

4A-4C (see also Charizanis, K., et al. (2012) Muscleblind-like 2-mediated alternative splicing in the developing brain and dysregulation in myotonic dystrophy. *Neuron* 75, 437-50; and Goodwin, M., et al. (2015) MBNL Sequestration by Toxic RNAs and RNA Misprocessing in the Myotonic Dystrophy Brain. *Cell Rep* 12, 1159-68). GABRG2 mis-splicing in DM may likely contribute to hypersomnia in myotonic dystrophy, as mice expressing the Gamma 2S isoform subunit of GABRG2 exclusively exhibit greater sleep times when treated with benzodiazepines as compared to those expressing normal ratios of 2L and 2S isoforms and show increased anxiety in the elevated plus maze (Quinlan, J. J., et al. (2000) Mice lacking the long splice variant of the gamma 2 subunit of the GABA(A) receptor are more sensitive to benzodiazepines. *Pharmacol. Biochem. Behav.* 66, 371-4).

$GABA_A$ receptors from gamma 2L deficient mice have increased affinity and behavioral sensitivity for benzodiazepine agonists (midazolam, diazepam, and zolpidem) (Id.). The action of midazolam in these mice is reversed by flumazenil. The GABRG2 2L/2S ratio may correlate with disease course/severity in DM.

MBNL2 knockout and DMSXL transgenic mouse models for myotonic dystrophy have increased frequency of spontaneous seizure and death in response to Pentylenetetrazole (PTZ), a non-competitive antagonist of the $GABA_A$ receptor. This implicates altered $GABA_A$ receptor function in the context of DM (Charizanis, K., et al. (2012) Muscleblind-like 2-mediated alternative splicing in the developing brain and dysregulation in myotonic dystrophy. *Neuron* 75, 437-50). Mbnl protein depletion is proposed to be an important mechanism occurring in DM1 brain that may cause symptoms such as hypersomnia, brain fog, and alterations to cognition. Mice lacking GABRG2 exon 9 show increased sensitivity to benzodiazepine treatment. The data described herein suggests that the decreased inclusion of GABRG2 exon 9 in human DM1 brain is mediated by Mbnl depletion, and therefore the hypothesis that there is an endozepine-like molecule that is present in DM CSF that mimics a benzodiazepine and that there is mis-splicing of the GABA receptor such that an isoform is created that is more sensitive to benzodiazepines may at least in part be mediated by Mbnl depletion due to sequestration by the expanded CUG/CCUG repeats that are expressed in DM1 tissues.

In contrast to pro-convulsant $GABA_A$ receptor antagonists such as PTZ (and also clarithromycin), flumazenil's pharmacological mechanism of action as a competitive antagonist and potentially inverse agonist renders it theoretically more safe and less likely to promote seizures in DM, This is because flumazenil specifically competes with endozepine-like molecules that hind to the benzodiazepine binding site on $GABA_A$ receptors, whereas PTZ and related molecules (e.g. clarithromycin or a fluoroquinolones) act as negative allosteric modulators that exhibit more generalized widespread effects on "intrinsic" GABA signaling. Therefore, in myotonic dystrophy, not only is there an endozepine(s)-like activity present in CSF, but the $GABA_A$ receptor whose activity may be modulated by the endozepine(s)-like activity is hypersensitive to this endozepine(s)-like activity.

In the context of myotonic dystrophy, flumazenil may yield clinical benefit via two distinct but connected mechanisms—lessening downstream effects of the hypersensitive $GABA_A$ receptor (caused by GABRG2 mis-splicing), as well as antagonizing the endozepine(s)-like activity from binding to the benzodiazepine binding site.

These benefits are the rationale for use of flumazenil or related drugs to improve "levels" of consciousness otherwise disaffected and manifesting as hypersomnia, unintended sleep, excessive daytime sleepiness, cognitive and arousal/alertness deficits in myotonic dystrophy types 1 and 2, including congenital myotonic dystrophy and forms with varying ages of onset. These benefits may apply to neuro-functional, neurodevelopmental, and neurodegenerative changes occurring in myotonic dystrophy.

Example 2

Prophetic

A patient can be identified as having DM1 myotonic dystrophy as confirmed by genetic testing and reports being sleepy. The patient will be asked to maintain a sleep log and to wear a wrist actigraphy device on his wrist. Follow up consultation will be conducted to eliminate potential causes of the patient's sleepiness such as sleep apnea and respiratory effort related arousal during nighttime sleep and to identify that the patient has hypersomnia or EDS.

Flumanzenil can be administered to the patient in a formulation similar to that as described in Rye et al., *Sci. Trans. Med.*, 2012, vol. 4, issue 161, pages 161ra151, for instance, in a sublingual formulation and/or transdermal formulation. Flumazenil can be administered in doses of 6-12 mg every 1.5 to 6 hours such that the total amount of flumazenil administered to subject does not exceed about 84 mg per day. The treatment can continue for at least 3 weeks. The effectiveness of the treatment can be assessed by the patient self-reporting, for instance, using the ESS.

Example 3

Figure 5:
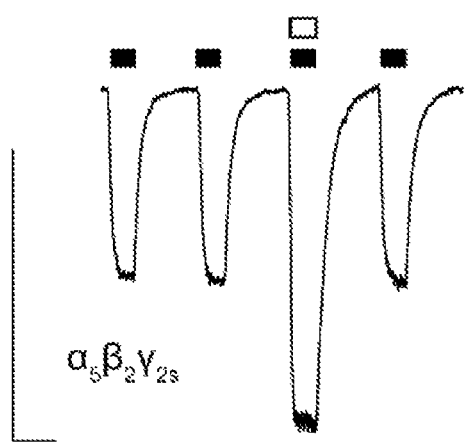
FIG. 5 shows α5β2Γ2s receptors are enhanced by DM1 CSF. Whole cell recording showing modulation and recovery from the effect of CSF. Filled boxes=GABA, open boxes=CSF.

DM1 CSF was shown to strongly enhance $GABA_A$ receptors containing the alpha5 subunit. This subunit is strongly expressed in the hippocampus and receptors continuing the alpha5 subunit are critical in controlling memory. Enhancement of alpha5-containing receptors by DM1 CSF is likely to contribute to the "brain-fog" experienced by patients with DM1 (FIG. 5).

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating hypersomnia and cognitive impairment associated with myotonic dystrophy in a human subject comprising, administering a therapeutically effective amount of flumazenil in the absence of pentylenetetrazol (PTZ) to the subject wherein the subject is diagnosed with myotonic dystrophy.

2. The method of claim 1, wherein flumazenil is administered to the subject by intravenous injection, intramuscular injection, subcutaneous injection, sublingual administration, inhalation, oral administration, transdermal administration, or a combination thereof.

3. The method of claim 2, wherein flumazenil is administered sublingually as a tablet, powder, film strip, capsule, lozenge, or troche.

4. The method of claim 2, wherein flumazenil is administered transdermally as an ointment, emulsion, lotion, cream, solution, gel, or patch.

5. The method of claim 2, wherein flumazenil is administered sublingually or transdermally.

6. The method of claim 1, wherein flumazenil is administered as a unit dose comprising from 5 mg to 40 mg.

7. The method of claim 1, wherein flumazenil is administered daily.

8. The method of claim 1, wherein the therapeutically effective amount is in an amount to reduce total habitual sleep time per day, compared to a subject that was not administered flumazenil.

9. The method of claim 1, wherein the therapeutically effective amount is in an amount to improve alertness, mental processing, and cognitive function, compared to a subject that was not administered flumazenil.

10. The method of claim 1, wherein the therapeutically effective amount is in an amount to improve the subject's processing speed by a factor of two or greater, as determined by the Symbol Digit Modalities Test, compared to a subject not being administered flumazenil.

* * * * *